United States Patent [19]
Bartmann et al.

[11] Patent Number: 5,705,095
[45] Date of Patent: Jan. 6, 1998

[54] PARTIALLY FLUORINATED BENZENE DERIVATIVES

[75] Inventors: Ekkehard Bartmann, Erzhausen; Ulrich Finkenzeller, Plankstadt, both of Germany

[73] Assignee: Merck Patent Gesellschaft Mit Beschrankter Haftung, Darmstadt, Germany

[21] Appl. No.: 600,107

[22] Filed: Feb. 12, 1996

[30] Foreign Application Priority Data

Feb. 11, 1995 [DE] Germany .................. 195 04 518.1

[51] Int. Cl.$^6$ .............. C09K 19/12; C09K 19/32; C09K 19/34; C07C 41/00
[52] U.S. Cl. .............. 252/299.66; 252/299.61; 252/299.62; 252/299.63; 252/299.65; 252/299.67; 568/647; 568/626
[58] Field of Search ............ 252/299.63, 299.66; 568/626, 647

[56] References Cited

U.S. PATENT DOCUMENTS 5,182,047  1/1993  Coates et al. ............... 252/299.66
5,273,680  12/1993  Gray et al. .................. 252/299.66
5,387,371  2/1995  Pausch et al. ............... 252/299.65

FOREIGN PATENT DOCUMENTS 6-228037  8/1994  Japan .

*Primary Examiner*—C. H. Kelly
*Attorney, Agent, or Firm*—Millen, White, Zelano, & Branigan, P.C.

[57] ABSTRACT

Compounds of the formula I

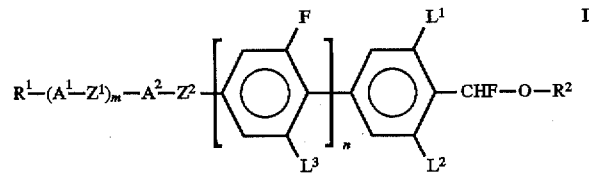

in which $R^1$, $R^2$, $A^1$, $A^2$, $Z^1$, $Z^2$, $L^1$, $L^2$, $L^3$, m and n are as defined herein, are suitable as component of liquid-crystalline media.

18 Claims, No Drawings

PARTIALLY FLUORINATED BENZENE DERIVATIVES

The invention relates to partially fluorinated benzene derivatives of the formula I:

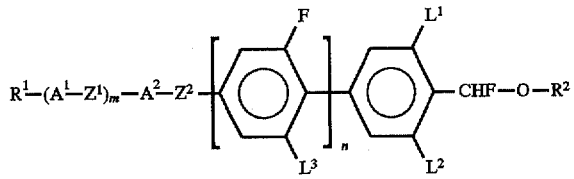

in which $R^1$ is H, an alkyl or alkenyl radical having 1 to 15 carbon atoms which is unsubstituted or monosubstituted by CN or $CF_3$ or, optionally, monosubstituted to perhalosubstituted by halogen, where, in addition, one or more $CH_2$ groups in these radicals may each, independently of one another, be replaced by —O—, —S—,

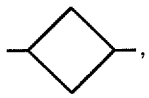

—CO—, —CO—O—, —O—CO— or —O—CO—O— in such a way that O atoms are not linked directly to one another, $A^1$ and $A^2$ are each, independently of one another, (a) a trans-1,4-cyclohexylene radical in which, in addition, one or more non-adjacent $CH_2$ groups may be replaced by —O— and/or —S—, (b) a 1,4-phenylene radical in which, in addition, one or two CH groups may be replaced by N, (c) a radical from the group consisting of 1,4-cyclohexenylene, 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) may be substituted by one or two fluorine atoms, $Z^1$ and $Z^2$ are each, independently of one another, —CO—O—, —O—CO—, —$CH_2$O—, —O$CH_2$—, —$CH_2CH_2$—, —CH=CH—, —C≡C—, —$(CH_2)_4$—, —CH=CH—$CH_2CH_2$— or a single bond, m is 0, 1 or 2, n is 0 or 1, $L^1$, $L^2$ and $L^3$ are each, independently of one another, H or F, and $R^2$ is an alkyl radical having 1 to 6 carbon atoms which is unsubstituted or substituted by one or more fluorine atoms, i.e., up to perhalo-substituted.

The invention furthermore relates to the use of these compounds as components of liquid-crystalline media, and to liquid-crystal and electro-optical display elements which contain the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

An object of the invention is providing novel stable liquid-crystalline or mesogenic compounds which are suitable as components of liquid-crystalline media and in particular simultaneously have relatively low viscosity and relatively high dielectric anisotropy.

It has now been found that compounds of the formula I are eminently suitable as components of liquid-crystalline media. In particular, they have comparatively low viscosities. They can be used to obtain stable liquid-crystalline media having a broad mesophase range and advantageous values for the optical and dielectric anisotropy. These media furthermore have very good low-temperature behavior.

In view of the wide variety of areas of application of such compounds of high Δε, however, it was desirable to have available further compounds of high nematogenity which have properties precisely customized to the particular applications.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials from which liquid-crystalline media are predominantly composed; however, compounds of the formula I can also be added to liquid-crystalline base materials from other classes of compounds in order, for example, to modify the dielectric and/or optical anisotropy of such composition and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystal display elements, in particular electro-optical display elements, which contain such media.

For reasons of simplicity, $A^4$ and $A^3$ below denote a radical of the formula

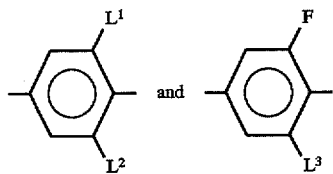

respectively, Cyc denotes a 1,4-cyclohexyl radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo[2.2.2]octylene radical, where Cyc and/or Phe may unsubstituted or monosubstituted or disubstituted by F or CN.

$A^1$ and $A^2$ are preferably selected from the group consisting of Cyc, Che, Phe, Pyr, Pyd and Dio.

Accordingly, the compounds of the formula I include bicyclic compounds of the subformulae Ia and Ib:

$R^1$—$A^2$—$A^4$—CHF—O—$R^2$   Ia $R^1$—$A^2$—$Z^2$—$A^4$—CHF—O—$R^2$   Ib tricyclic compounds of the subformulae Ic to Ig R¹—A¹—A²—A⁴—CHF—O—R²  Ic R¹—A¹—Z¹—A²—A⁴—CHF—O—R²  Id R¹—A¹—A²—Z²—A⁴—CHF—O—R²  Ie R¹—A¹—A³—A⁴—CHF—O—R²  If R¹—A¹—Z¹—A³—A⁴—CHF—O—R²  Ig and tetracyclic compounds of the subformulae Ih to Ik:

R¹—A¹—A²—A³—A⁴—CHF—O—R²  Ih

R¹—A¹—Z¹—A²—A³—A⁴—CHF—O—R²  Ii

R¹—A¹—A²—Z²—A³—A⁴—CHF—O—R²  Ij

R¹—A¹—Z¹—A²—Z²—A³—A⁴—CHF—O—R²  Ik

R² is preferably —CF₃, —CH₂CF₃, —CH₂CHF₂, —CH₂CH₂F, —CF₂CHF₂, —CF₂CH₂F, —CHFCH₃, —CF₂CF₃, —CH₂—CF₂—CHF₂, —CH₂C₂F₅, —CHFCHF₂, C₂H₅ or C₃H₇.

Preference is also given to compounds of the formula I and of all subformulae in which A¹, A², A³ and/or A⁴ is 1,4-phenylene which is monosubstituted or disubstituted by F. These are, in particular, 2-fluoro-1,4-phenylene, 3-fluoro-1,4-phenylene and 3,5-difluoro-1,4-phenylene.

A¹ and A² are independently preferably

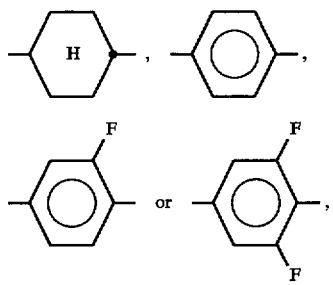

Z¹ and Z² are independently preferably a single bond, —CO—O—, —O—CO— or —CH₂CH₂—, secondarily preferably —CH₂O— and —OCH₂—. If one of the radicals Z¹ and Z² is —(CH₂)₄— or —CH=CH—CH₂CH₂—, the other radical Z¹ or Z² (if present) is preferably a single bond.

m and n are preferably 1 or 0, particular preference being given to compounds in which m+n=1.

If R¹ is an alkyl radical and/or alkoxy radical, this may be straight-chain or branched. It is preferably straight-chain, has 2, 3, 4, 5, 6 or 7 carbon atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R¹ is an alkyl radical in which one CH₂ group has been replaced by —CH=CH—, this may be straight-chain or branched. It is preferably straight-chain and has 2 to 10 carbon atoms. It is accordingly particularly vinyl, prop-1- or -2-enyl, but-1-, -2- or -3-enyl, pent-1-, -2-, -3- or -4-enyl, hex-1-, -2-, -3-, -4- or -5- enyl, hept- 1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R¹ is an alkyl radical in which one CH₂ group has been replaced by —O— and one has been replaced by —CO—, these are preferably adjacent. It thus contains one acyloxy group —CO—O— or one oxycarbonyl group —O—CO—. It is preferably straight-chain and has 2 to 6 carbon atoms. It is accordingly particularly acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R¹ is an alkyl radical in which one CH₂ group has been replaced by unsubstituted or substituted —CH=CH— and an adjacent CH₂ group has been replaced by CO or CO—O or O—CO—, it may be straight-chain or branched. It is preferably straight-chain and has 4 to 13 carbon atoms. It is accordingly particularly acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R¹ is an alkyl or alkenyl radical which is monosubstituted by CN or CF₃, this radical is preferably straight-chain and the substitution by CN or CF₃ is in the ω-position.

If R¹ is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but is preferably in the ω-position.

Compounds of the formula I which contain wing groups R¹ and/or R² which are suitable for addition polymerization reactions are suitable for the preparation of liquid-crystalline polymers.

Compounds of the formula I containing branched wing groups R¹ and/or R² may occasionally be of importance due to better solubility in the customary liquid-crystalline base materials, but in particular as chiral dopes if they are optically active. Smectic compounds of this type are suitable as components for ferroelectric materials.

Compounds of the formula I having S_A phases are suitable, for example, for thermally addressed displays.

Branched groups of this type generally contain not more than one chain branch. Preferred branched radicals R¹ and/or R² are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R¹ is an alkyl radical in which two or more CH₂ groups have been replaced by —O— and/or —CO—O—, it may be straight-chain or branched. It is preferably branched and has 3 to 12 carbon atoms. It is accordingly particularly biscarboxymethyl, 2,2-biscarboxyethyl, 3,3-bis-carboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)pentyl.

Compounds of the formula I which contain wing groups $R^1$ which are suitable for polycondensations are suitable for the preparation of liquid-crystalline polycondensates.

The formula I covers the racemates of these compounds and the optical antipodes, and mixtures thereof.

Of these compounds of the formula I and of the sub-formulae, preference is given to those in which at least one of the radicals present therein has one of the preferred meanings given.

In the compounds of the formula I, preferred stereoisomers are those in which the rings Cyc and piperidine are trans-1,4-disubstituted. Those of the abovementioned formulae which contain one or more Pyd, Pyr and/or Dio groups in each case include the two 2,5-positional isomers.

Preferred smaller groups of compounds are those of the subformulae I1 to I21:

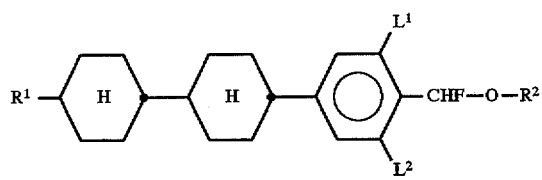

I1

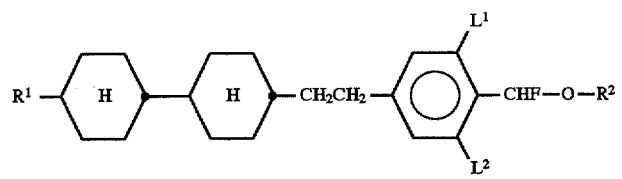

I2

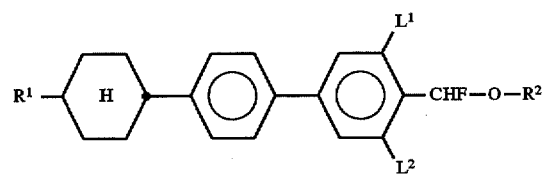

I3

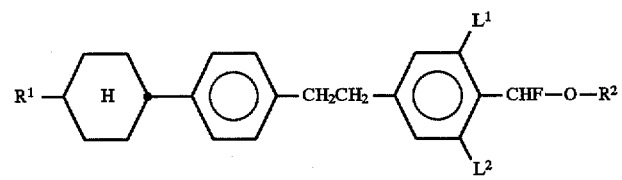

I4

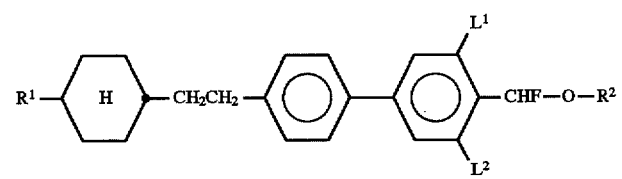

I5

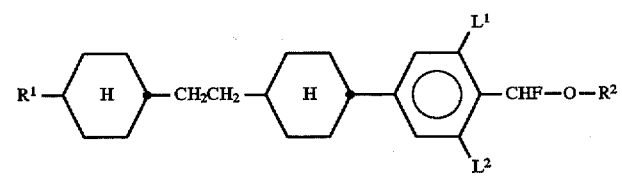

I6

-continued
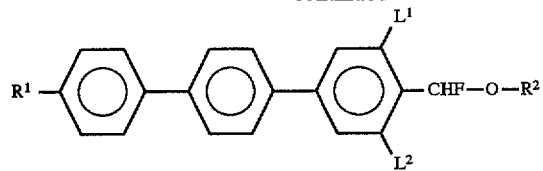 I7
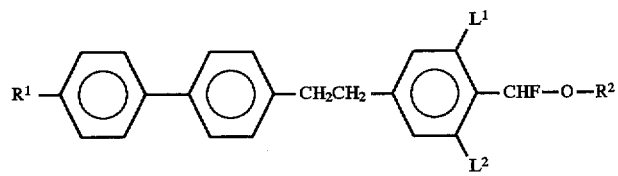 I8
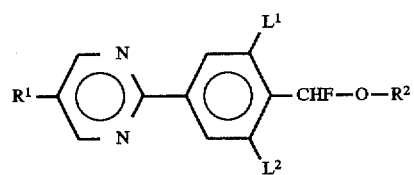 I9
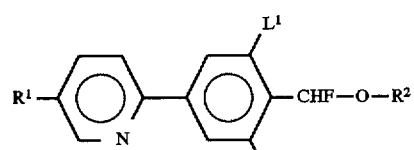 I10
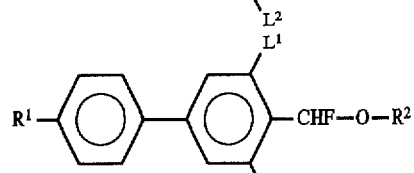 I11
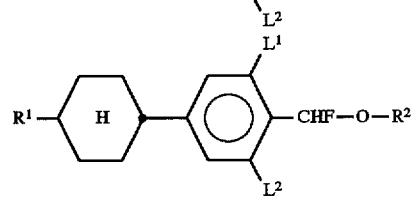 I13
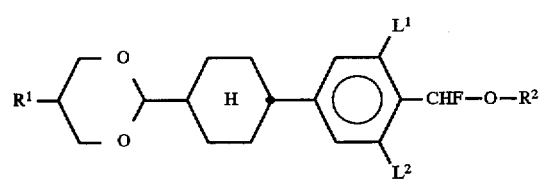 I14
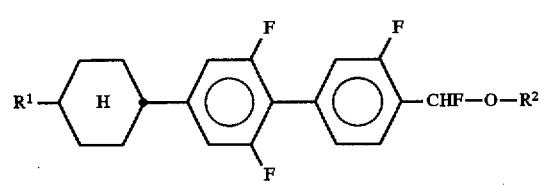 I15
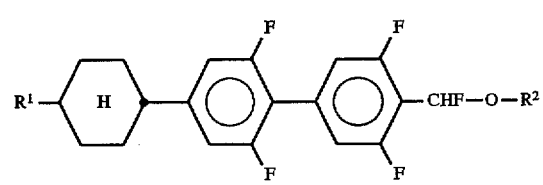 I16

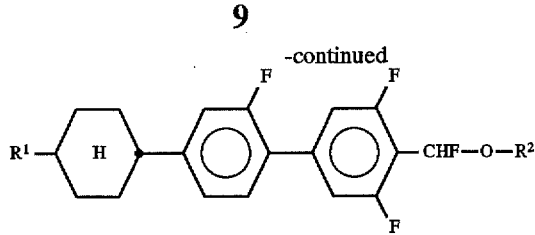 I17

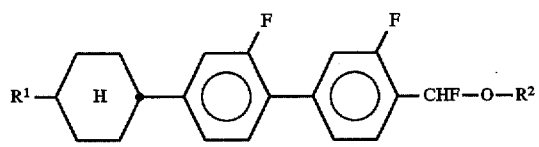 I18

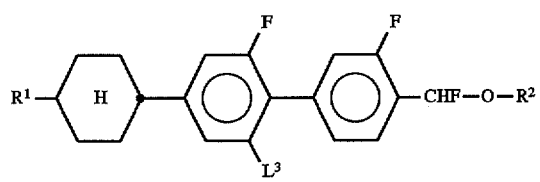 I19

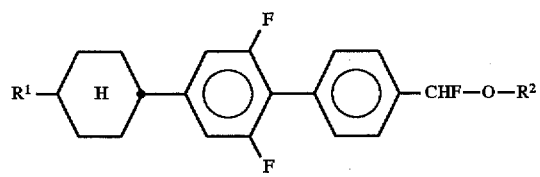 I20

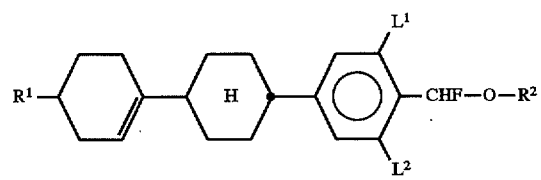 I21

The 1,4-cyclohexenylene group preferably has one of the following structures:

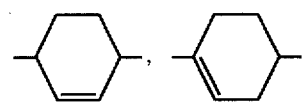

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions.

Use can also be made here of variants which are known per se, but are not mentioned here in greater detail.

The novel compounds can be prepared, for example, as follows:

Scheme 1

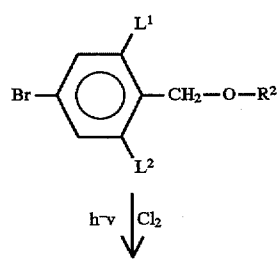

-continued
Scheme 1

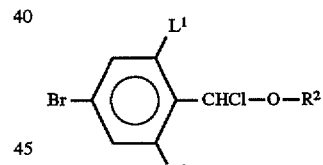

↓ KF/DMEU

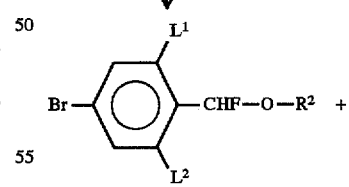 +

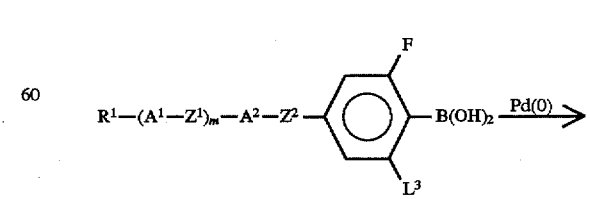

Scheme 1

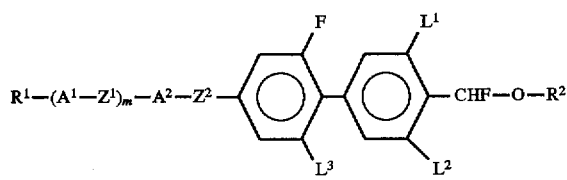

Scheme 2

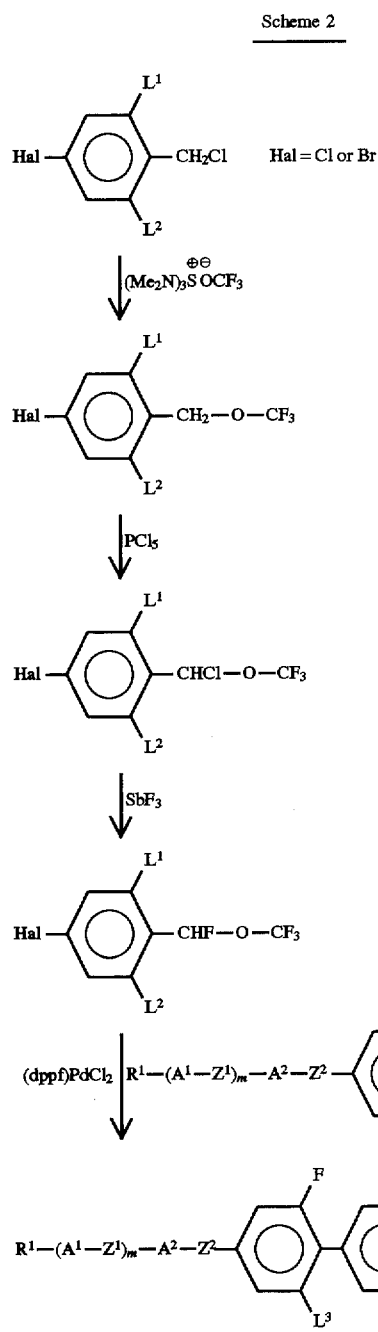

Scheme 3

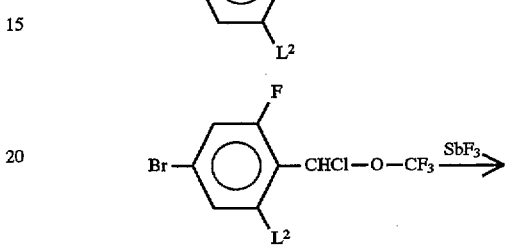

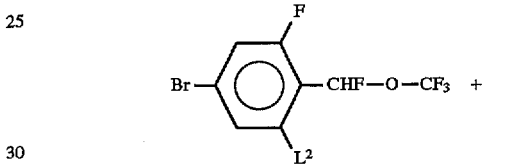

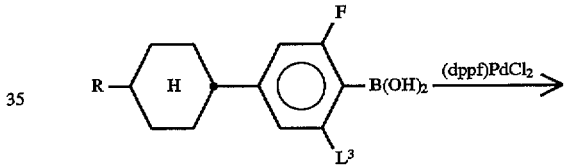

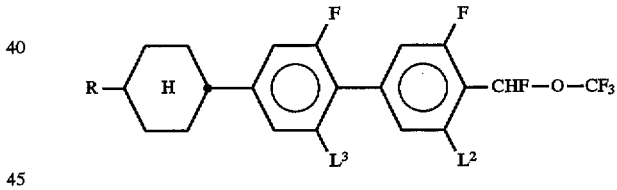

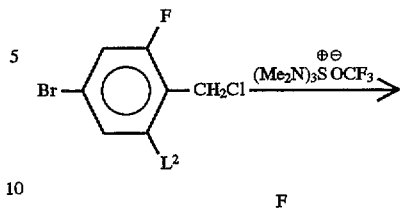

The invention also relates to the intermediates of the formula

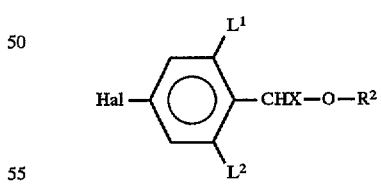

in which Hal is Cl or Br, X is H, F or Cl, and $L^1$, $L^2$ and $R^2$ are as defined in claim 1.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylthanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

$$R'—L—E—R'' \qquad 1$$

$$R'—L—COO—E—R'' \qquad 2$$

$$R'—L—OOC—E—R'' \qquad 3$$

$$R'—L—CH_2CH_2—E—R'' \qquad 4$$

$$R'—L—C\equiv C—E—R'' \qquad 5$$

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R'' are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the subformulae 1a, 2a, 3a, 4a and 5a. In most of these compounds, R' and R'' are different from one another, one of these radicals usually being alkyl, alkenyl, alkoxy or alkoxyalkyl.

In another smaller sub-group of the compounds of the formulae 1, 2, 3, 4 and 5 which is known as group B, R'' is —F, —Cl, —NCS or —(O)$_i$CH$_{3-(k+1)}$F$_k$Cl$_1$, where i is 0 or 1, and k+1 is 1, 2 or 3; the compounds in which R'' has this meaning are labelled with the subformulae 1b, 2b, 3b, 4b and 5b. Particular preference is given to those compounds of the sub formulae 1b, 2b, 3b, 4b and 5b in which R'' is —F, —Cl, —NCS, —CF$_3$, —OCHF$_2$ or —OCF$_3$.

In the compounds of the subformulae 1b, 2b, 3b, 4b and 5b, R' is as defined for the compounds of the subformulae 1a–5a and is preferably alkyl, alkenyl, alkoxy or alkoxyalkyl.

In a further smaller sub-group of the compounds of the formulae 1, 2, 3, 4 and 5, R'' is —CN; this sub-group is called group C below, and the compounds of this sub-group are correspondingly described by subformulae 1c, 2c, 3c, 4c and 5c. In the compounds of the subformulae 1c, 2c, 3c, 4c and 5c, R' is as defined for the compounds of the subformulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5 to 90% and in particular 10 to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the present application and in the examples below, the structures of the liquid-crystal compounds are indicated by acronyms, the transformation into chemical formulae taking place as in Tables A and B below. All the radicals $C_nH_{2n+1}$ and $C_mH_{2m+1}$ are straight-chain alkyl radicals containing n or m carbon atoms respectively. The coding in Table B is self-evident. In Table A, only the acronym for the parent structure is given. In individual cases, the acronym for the parent structure is followed, separated from it by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |

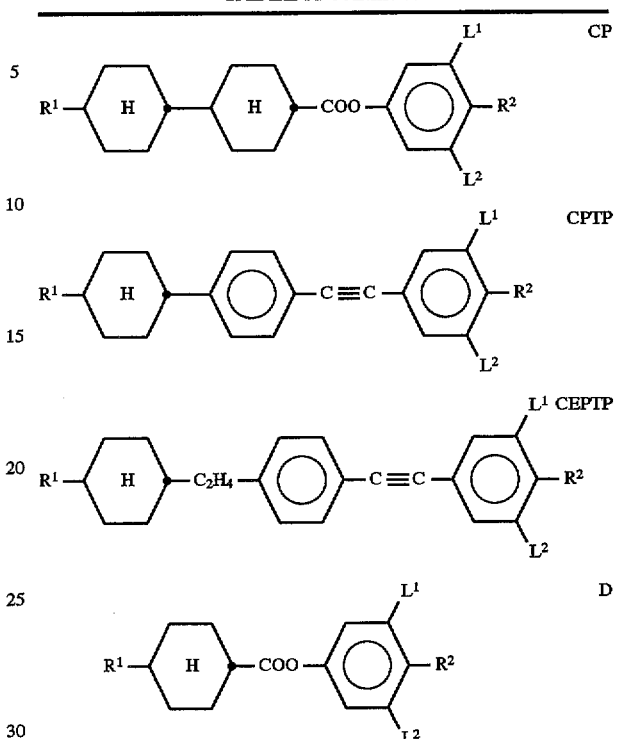

TABLE A

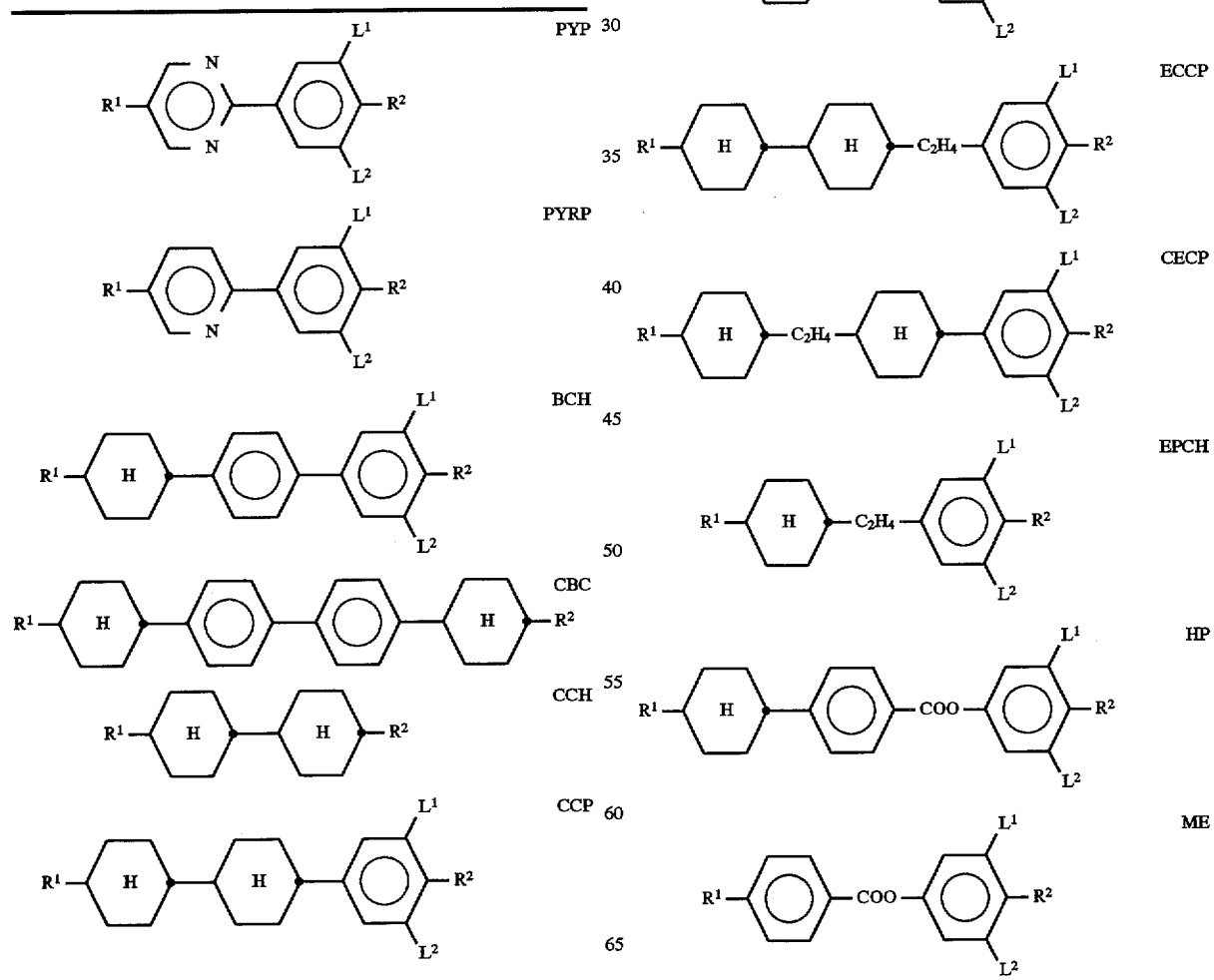

TABLE A-continued

TABLE A-continued
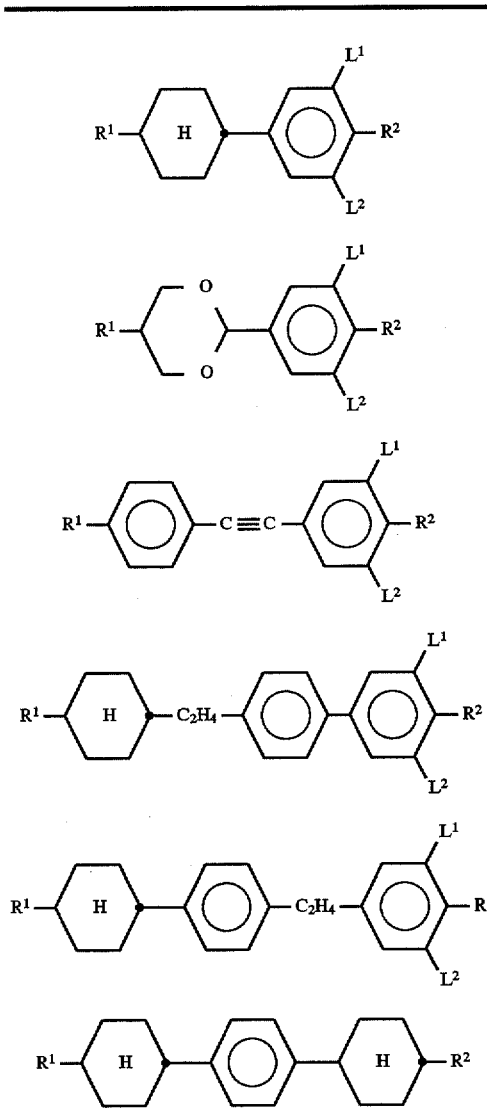
PCH
PDX
PTP
BECH
EBCH
CPC
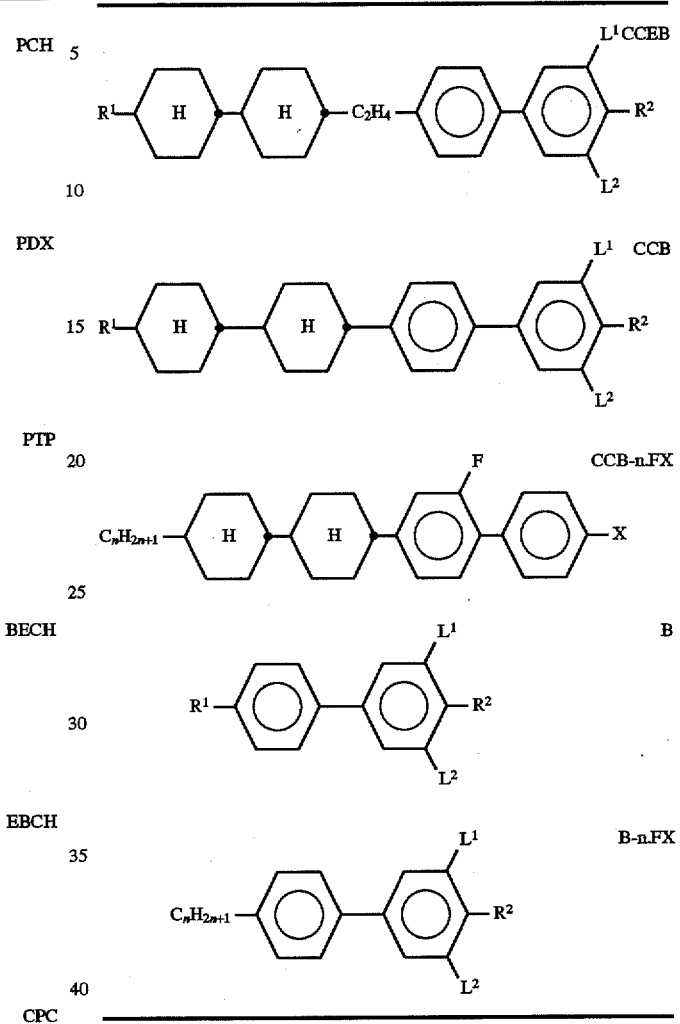
L¹CCEB
CCB
CCB-n.FX
B
B-n.FX
TABLE B
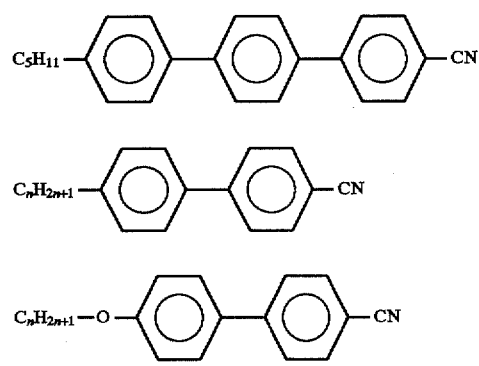
T15
K3n
M3n

TABLE B-continued

| Structure | Code |
|---|---|
| $C_nH_{2n+1}$—[H]—[Ph-F]—[Ph]—X | BCH-n.FX |
| $C_nH_{2n+1}$—[H]—$C_2H_4$—[Ph]—[Ph-F]—$C_mH_{2m+1}$ | Inm |
| $C_nH_{2n+1}$—[H]—[H]—OCC—$C_mH_{2m+1}$ | C-nm |
| $C_2H_5$—CH(CH$_3$)*—CH$_2$—O—[Ph]—[Ph]—CN | C15 |
| $C_2H_5$—CH(CH$_3$)*—CH$_2$—[Ph]—[Ph]—CN | CB15 |
| $C_nH_{2n+1}$—[H]—[Ph]—[Ph-F]—[H]—$C_mH_{2m+1}$ | CBC-nmF |
| $C_nH_{2n+1}$—[H]—[H]—COO—[Ph]—[H]—$C_mH_{2m+1}$ | CCPC-nm |
| $C_nH_{2n+1}$—[H]—[H]—COO—[H]—$C_mH_{2m+1}$ | CH-nm |
| $C_nH_{2n+1}$—[H]—[Ph]—COO—[H]—$C_mH_{2m+1}$ | HH-nm |
| $C_nH_{2n+1}$—[H]—COO—[H]—$C_mH_{2m+1}$ | OS-nm |
| $C_nH_{2n+1}$—[H]—$C_2H_4$—[Ph]—[Ph]—[H]—$C_mH_{2m+1}$ | ECBC-nm |
| $C_nH_{2n+1}$—[Ph]—[Ph-F]—[Ph]—CN | T-nFN |
| $C_nH_{2n+1}$—[H]—[H]—[Ph-F,F,F] | CCP-nF.F.F |

TABLE B-continued

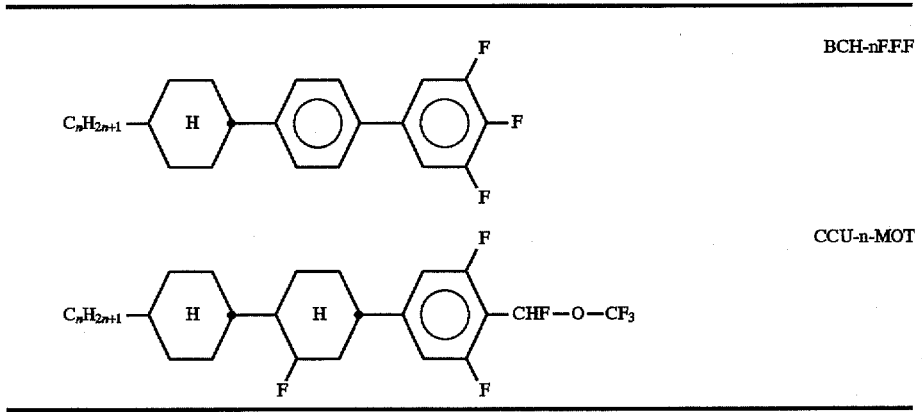

BCH-nF.F.F

CCU-n-MOT

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding German application No. P 95 04 518.1, filed Feb. 11, 1995, is hereby incorporated by reference.

EXAMPLES

The examples below are intended to illustrate the invention without representing a limitation. Above and below, percentages are percent by weight. All temperatures are given in degrees Celsius. mp.=melting point, cp.=clear point. Furthermore, C=crystalline state, N=nematic phase, S=smectic phase and I=isotropic phase. The numbers between these symbols indicate the conversion temperatures. Δn denotes optical anisotropy (589 nm, 20° C.), and the viscosity (mm²/sec) was determined at 20° C.

"Conventional work-up" means that water is added if necessary, the mixture is extracted with dichloromethane, diethyl ether, methyl tert-butyl ether or toluene, the organic phase is separated off, dried and evaporated, and the product is purified by distillation under reduced pressure or crystallization and/or chromatography. The following abbreviations are used:

| | |
|---|---|
| DAST | diethylaminosulfur trifluoride |
| DMEU | 1,3-dimethyl-2-imidazolidinone |
| POT | potassium tertiary-butanolate |
| THF | tetrahydrofuran |
| pTsOH | p-toluenesulfonic acid |

Example 1

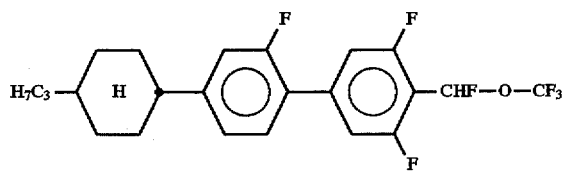

Step 1.1

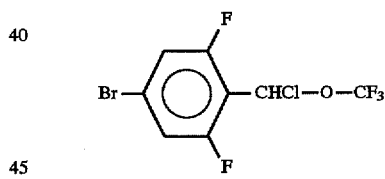

40 mmol of (4-bromo-2,6-difluorophenyl)chloromethane and 40 mmol of trisdimethylaminosulfonium trifluoromethoxide are dissolved in 100 ml of dichloromethane. The solution is stirred at 0° C. for 4 days and then evaporated in vacuo. The residue is taken up in ether, and the mixture is extracted with water. The organic phase is evaporated in vacuo. The product is isolated from the residue by chromatography.

Step 1.2

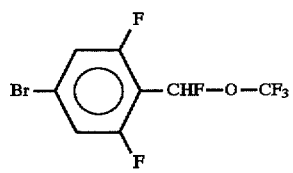

20 mmol of (4-bromo-2,6-difluorophenyl)methyl trifluoromethyl ether are warmed to 140° C. for 15 hours with 20 mmol of phosphorus pentachloride. After cooling to 0° C., the mixture is hydrolyzed by the addition of ice-water and extracted with dichloromethane. The combined organic phases are evaporated in vacuo. The product is isolated from the residue by chromatography.

Step 1.3

10 mmol of (4-bromo-2,6-difluorophenyl)chloromethyl trifluoromethyl ether are warmed to 120° C. for 15 hours with 25 mmol of antimony trifluoride. After cooling to 0° C., the mixture is hydrolyzed by the addition of 100 ml of 10% hydrochloric acid and extracted with dichloromethane. The organic phase is evaporated in vacuo. The product is isolated from the residue by chromatography.

Step 1.4

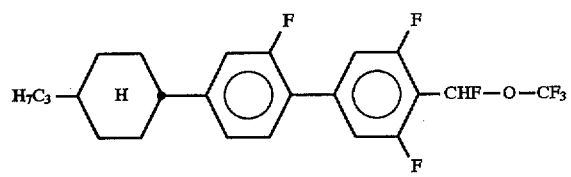

A solution of 5 mmol of (4-bromo-2,6-difluorophenyl) fluoromethyl trifluoromethyl ether and 0.15 g of (bisdiphenylphosphineferrocene)palladium chloride in 15 ml of toluene is mixed with a solution of 5 mmol of 2-fluoro-4-(4-propylcyclohexyl)benzeneboronic acid in 10 ml of ethanol. A solution of 2.5 g of $Na_2CO_3$ in 10 ml of water is then added. The mixture is then refluxed for 3 hours with vigorous stirring. After cooling to room temperature, the mixture is acidified by means of dilute hydrochloric acid. The aqueous phase is separated off and extracted with toluene. The combined organic phases are evaporated in vacuo, and the residue is subjected to column chromatography on silica gel using hexane as eluent. The eluate is evaporated in vacuo, and the residue is recrystallized twice.

The following compounds of the formula

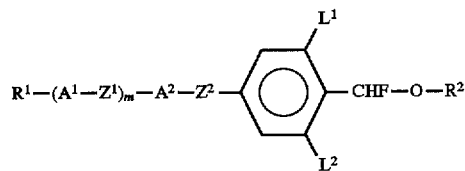

are prepared analogously:

| $R^1$ | $-(A^1-Z^1)_m-A^2-Z^2-$ | $L^1$ | $L^2$ | $R^2$ |
|---|---|---|---|---|
| $C_3H_7$ | -[H]- | F | H | $CF_3$ |
| $C_5H_{11}$ | -[H]- | F | H | $CF_3$ |
| $CH_3$ | -[H]- | H | H | $CF_3$ |
| $C_2H_5$ | -[H]-[H]- | H | F | $CF_3$ |
| $n-C_3H_7$ | -[H]-[H]- | H | H | $CF_3$ |
| $n-C_3H_7$ | -[H]-[H]- | H | F | $CF_3$ |
| $n-C_3H_7$ | -[H]-[H]- | F | F | $CF_3$ |
| $n-C_4H_9$ | -[H]-[H]- | H | H | $CF_3$ |
| $n-C_4H_9$ | -[H]-[H]- | H | F | $CF_3$ |
| $n-C_4H_9$ | -[H]-[H]- | F | F | $CF_3$ |
| $n-C_5H_{11}$ | -[H]-[H]- | H | H | $CF_3$ |
| $n-C_5H_{11}$ | -[H]-[H]- | H | F | $CF_3$ |
| $n-C_5H_{11}$ | -[H]-[H]- | F | F | $CF_3$ |
| $n-C_6H_{13}$ | -[H]-[H]- | H | H | $CF_3$ |
| $n-C_6H_{13}$ | -[H]-[H]- | H | F | $CF_3$ |
| $n-C_6H_{13}$ | -[H]-[H]- | F | F | $CF_3$ |
| $CH_3$ | -[H]-[Ph]- | F | F | $CF_3$ |
| $C_2H_5$ | -[H]-[Ph]- | F | F | $CF_3$ |
| $n-C_3H_7$ | -[H]-[Ph]- | H | H | $CF_3$ |
| $n-C_3H_7$ | -[H]-[Ph]- | H | F | $CF_3$ |

-continued

| R¹ | −(A¹−Z¹)$_m$−A²−Z²− | L¹ | L² | R² |
|---|---|---|---|---|
| n-C₃H₇ | cyclohexyl–phenyl– | F | F | CF₃ |
| n-C₄H₉ | cyclohexyl–phenyl– | H | F | CF₃ |
| n-C₅H₁₁ | cyclohexyl–phenyl– | H | H | CF₃ |
| n-C₅H₁₁ | cyclohexyl–phenyl– | H | F | CF₃ |
| n-C₅H₁₁ | cyclohexyl–phenyl– | F | F | CF₃ |
| C₂H₅ | cyclohexyl–(3-F)phenyl– | H | H | CF₃ |
| C₂H₅ | cyclohexyl–(3-F)phenyl– | H | F | CF₃ |
| C₂H₅ | cyclohexyl–(3-F)phenyl– | F | F | CF₃ |
| n-C₃H₇ | cyclohexyl–(3-F)phenyl– | H | H | CF₃ |
| n-C₃H₇ | cyclohexyl–(3-F)phenyl– | H | F | CF₃ |
| n-C₃H₇ | cyclohexyl–(3-F)phenyl– | F | F | CF₃ |
| n-C₄H₉ | cyclohexyl–(3-F)phenyl– | F | F | CF₃ |
| n-C₅H₁₁ | cyclohexyl–(3-F)phenyl– | H | H | CF₃ |
| n-C₅H₁₁ | cyclohexyl–(3-F)phenyl– | H | F | CF₃ |
| n-C₅H₁₁ | cyclohexyl–(3-F)phenyl– | F | F | CF₃ |
| n-C₆H₁₃ | cyclohexyl–(3-F)phenyl– | H | F | CF₃ |
| C₂H₅ | cyclohexyl–(3,5-diF)phenyl– | H | H | CF₃ |
| C₂H₅ | cyclohexyl–(3,5-diF)phenyl– | H | F | CF₃ |
| C₂H₅ | cyclohexyl–(3,5-diF)phenyl– | F | F | CF₃ |
| n-C₃H₇ | cyclohexyl–(3,5-diF)phenyl– | H | H | CF₃ |
| n-C₃H₇ | cyclohexyl–(3,5-diF)phenyl– | H | F | CF₃ |

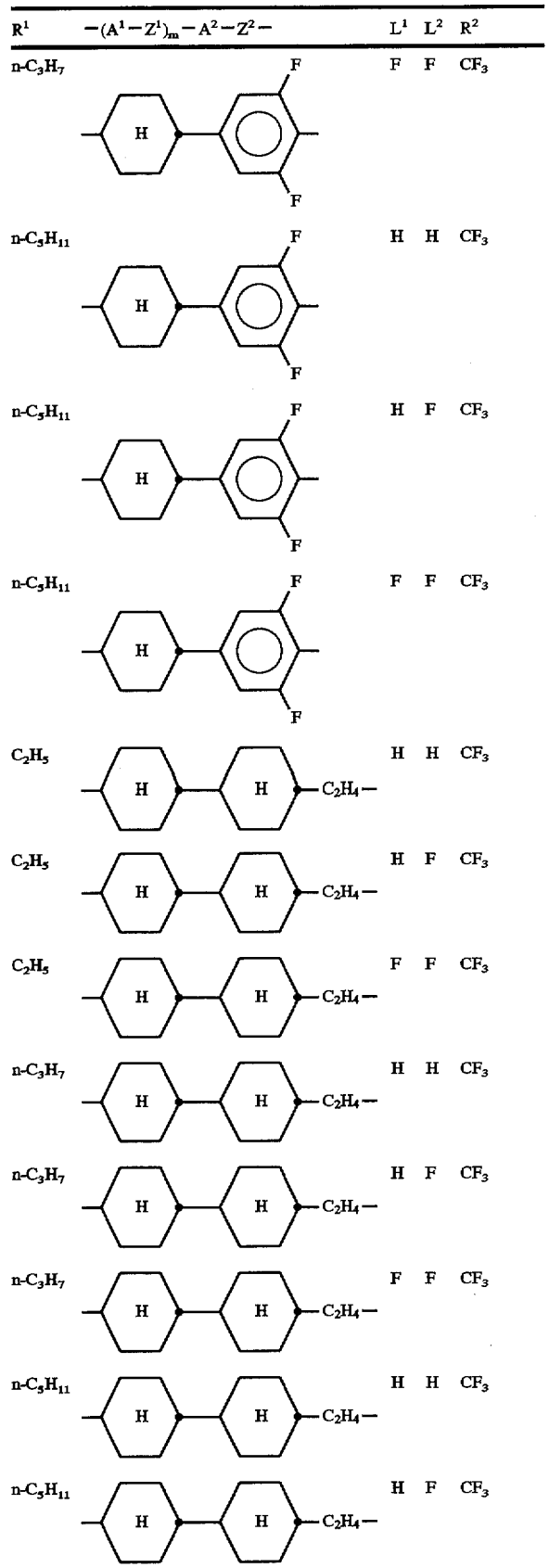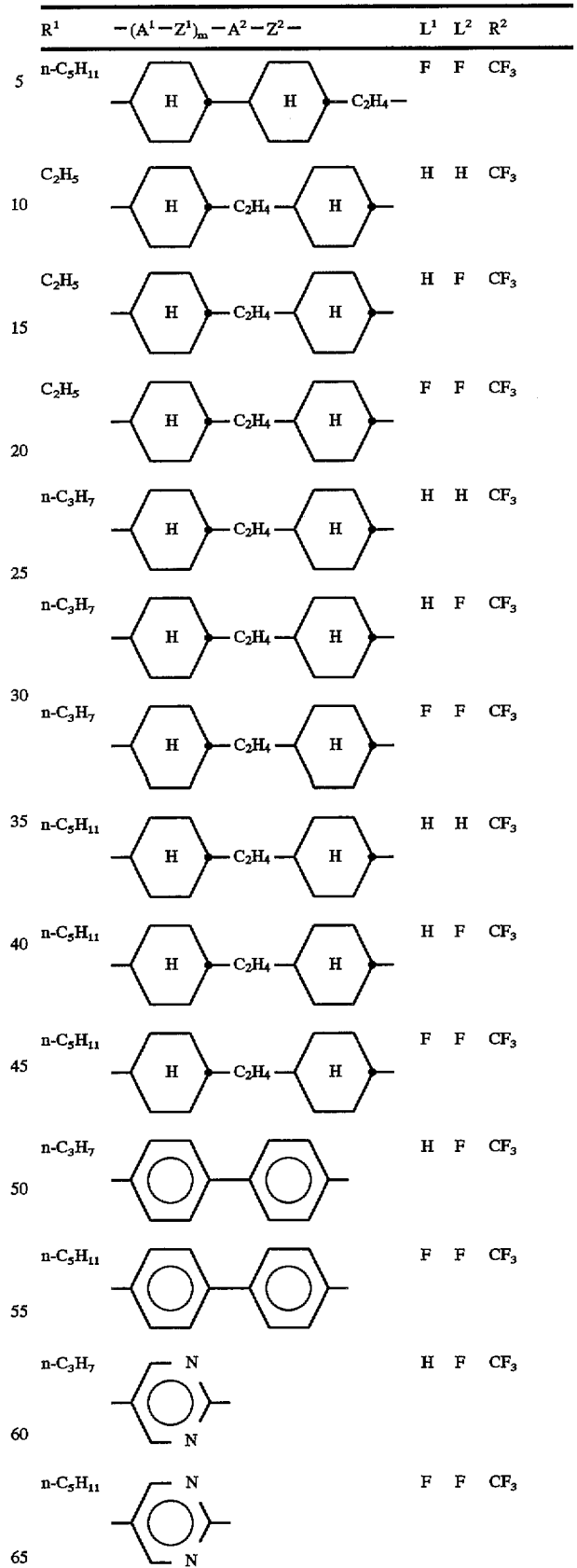

| R¹ | −(A¹−Z¹)ₘ−A²−Z²− | L¹ | L² | R² |
|---|---|---|---|---|
| n-C₃H₇ | 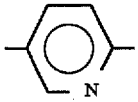 | H | F | CF₃ |
| n-C₅H₁₁ | 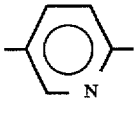 | F | F | CF₃ |
| n-C₃H₇ | 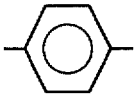 | H | F | CF₃ |
| n-C₅H₁₁ | 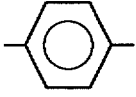 | F | F | CF₃ |
| n-C₃H₇ | 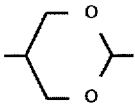 | H | F | CF₃ |
| n-C₅H₁₁ | 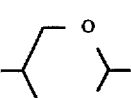 | F | F | CF₃ |
| n-C₃H₇ | 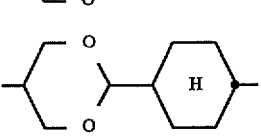 | H | F | CF₃ |
| n-C₅H₁₁ | 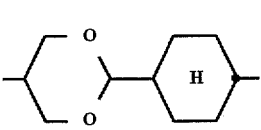 | F | F | CF₃ |
| n-C₃H₇ | 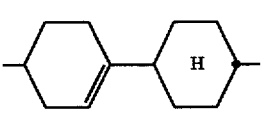 | H | F | CF₃ |
| n-C₅H₁₁ | 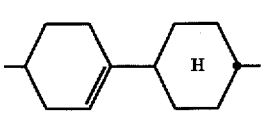 | F | F | CF₃ |
| n-C₃H₇ | 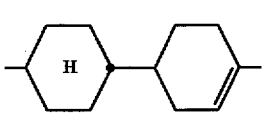 | H | F | CF₃ |
| n-C₅H₁₁ | 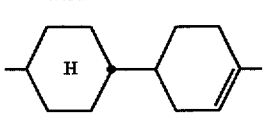 | F | F | CF₃ |
| C₂H₅ | 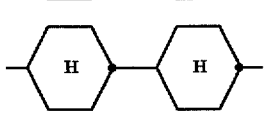 | H | H | CH₂CF₃ |
| C₂H₅ | 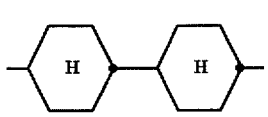 | H | F | CH₂CF₃ |
| C₂H₅ | 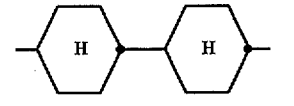 | F | F | CH₂CF₃ |
| n-C₃H₇ | 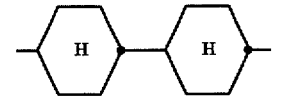 | H | H | CH₂CF₃ |
| n-C₃H₇ | 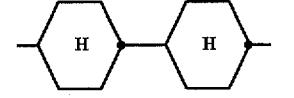 | H | F | CH₂CF₃ |
| n-C₃H₇ | 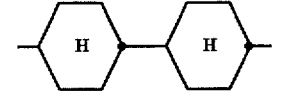 | F | F | CH₂CF₃ |
| n-C₅H₁₁ | 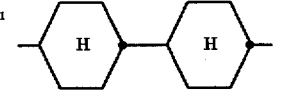 | H | H | CH₂CF₃ |
| n-C₅H₁₁ | 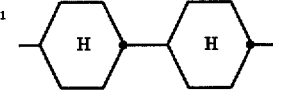 | H | F | CH₂CF₃ |
| n-C₅H₁₁ | 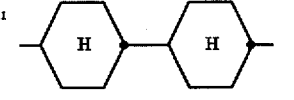 | F | F | CH₂CF₃ |
| C₂H₅ | 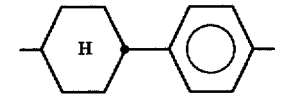 | H | H | CH₂CF₃ |
| C₂H₅ | 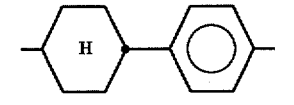 | H | F | CH₂CF₃ |
| C₂H₅ | 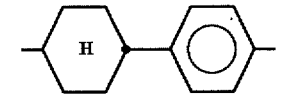 | F | F | CH₂CF₃ |
| n-C₃H₇ | 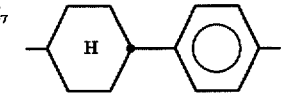 | H | H | CH₂CF₃ |
| n-C₃H₇ | 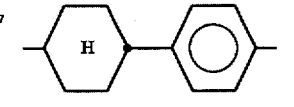 | H | F | CH₂CF₃ |
| n-C₃H₇ | 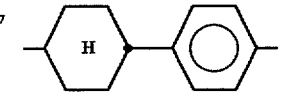 | F | F | CH₂CF₃ |
| n-C₅H₁₁ | 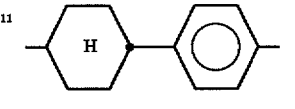 | H | H | CH₂CF₃ |
| n-C₅H₁₁ | 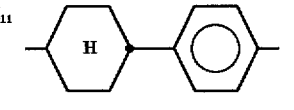 | H | F | CH₂CF₃ |

-continued

| R¹ | -(A¹-Z¹)ₘ-A²-Z²- | L¹ | L² | R² |
|---|---|---|---|---|
| n-C₅H₁₁ | cyclohexyl-phenyl (4-F) | F | F | CH₂CF₃ |
| C₂H₅ | cyclohexyl-phenyl (3-F) | H | H | CH₂CF₃ |
| C₂H₅ | cyclohexyl-phenyl (3-F) | H | F | CH₂CF₃ |
| C₂H₅ | cyclohexyl-phenyl (2,3-diF) | F | F | CH₂CF₃ |
| n-C₃H₇ | cyclohexyl-phenyl (3-F) | H | H | CH₂CF₃ |
| n-C₃H₇ | cyclohexyl-phenyl (3-F) | H | F | CH₂CF₃ |
| n-C₃H₇ | cyclohexyl-phenyl (2,3-diF) | F | F | CH₂CF₃ |
| n-C₅H₁₁ | cyclohexyl-phenyl (3-F) | H | H | CH₂CF₃ |
| n-C₅H₁₁ | cyclohexyl-phenyl (3-F) | H | F | CH₂CF₃ |
| n-C₅H₁₁ | cyclohexyl-phenyl (2,3-diF) | F | F | CH₂CF₃ |
| C₂H₅ | cyclohexyl-phenyl (3,5-diF) | H | H | CH₂CF₃ |

-continued

| R¹ | -(A¹-Z¹)ₘ-A²-Z²- | L¹ | L² | R² |
|---|---|---|---|---|
| C₂H₅ | cyclohexyl-phenyl (3,5-diF) | H | F | CH₂CF₃ |
| C₂H₅ | cyclohexyl-phenyl (3,5-diF) | F | F | CH₂CF₃ |
| n-C₃H₇ | cyclohexyl-phenyl (3,5-diF) | H | H | CH₂CF₃ |
| n-C₃H₇ | cyclohexyl-phenyl (3,5-diF) | H | F | CH₂CF₃ |
| n-C₃H₇ | cyclohexyl-phenyl (3,5-diF) | F | F | CH₂CF₃ |
| n-C₅H₁₁ | cyclohexyl-phenyl (3,5-diF) | H | H | CH₂CF₃ |
| n-C₅H₁₁ | cyclohexyl-phenyl (3,5-diF) | H | F | CH₂CF₃ |
| n-C₅H₁₁ | cyclohexyl-phenyl (3,5-diF) | F | F | CH₂CF₃ |
| n-C₃H₇ | cyclohexyl-cyclohexyl-C₂H₄- | H | H | CH₂CF₃ |

| R¹ | −(A¹−Z¹)ₘ−A²−Z²− | L¹ | L² | R² |
|---|---|---|---|---|
| n-C₃H₇ | 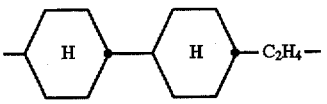 | H | F | CH₂CF₃ |
| n-C₃H₇ | 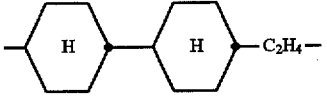 | F | F | CH₂CF₃ |
| n-C₅H₁₁ | 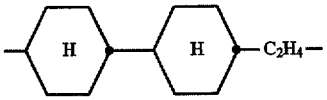 | H | H | CH₂CF₃ |
| n-C₅H₁₁ | 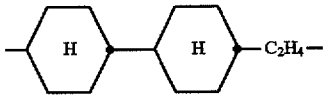 | H | F | CH₂CF₃ |
| n-C₅H₁₁ | 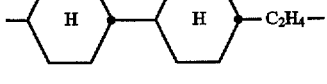 | F | F | CH₂CF₃ |
| n-C₃H₇ | 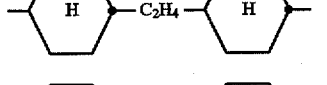 | H | H | CH₂CF₃ |
| n-C₃H₇ | 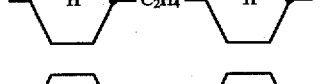 | H | F | CH₂CF₃ |
| n-C₃H₇ |  | F | F | CH₂CF₃ |
| n-C₅H₁₁ |  | H | H | CH₂CF₃ |
| n-C₅H₁₁ |  | H | F | CH₂CF₃ |
| n-C₅H₁₁ |  | F | F | CH₂CF₃ |
| C₂H₅ | 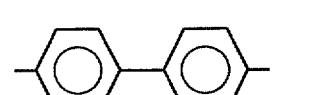 | H | H | CH₂CF₃ |
| n-C₃H₇ | 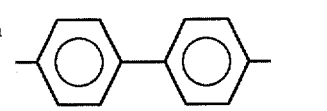 | H | F | CH₂CF₃ |
| n-C₅H₁₁ |  | F | F | CH₂CF₃ |
| C₂H₅ | 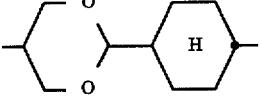 | H | H | CH₂CF₃ |
| n-C₃H₇ | 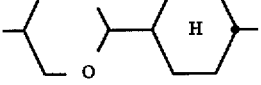 | H | F | CH₂CF₃ |
| n-C₅H₁₁ | 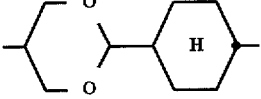 | F | F | CH₂CF₃ |
| C₂H₅ | 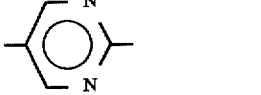 | H | H | CH₂CF₃ |
| n-C₃H₇ | 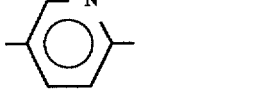 | H | F | CH₂CF₃ |
| n-C₅H₁₁ | 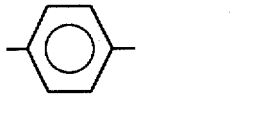 | F | F | CH₂CF₃ |
| n-C₃H₇ | 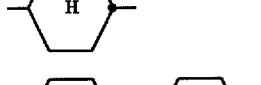 | F | F | CH₂CF₃ |
| C₂H₅ |  | H | H | CH₂CH₂F |
| C₂H₅ |  | H | F | CH₂CH₂F |
| C₂H₅ | 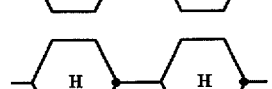 | F | F | CH₂CH₂F |
| n-C₃H₇ | 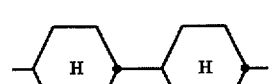 | H | H | CH₂CH₂F |
| n-C₃H₇ | 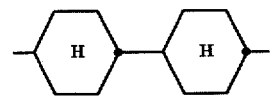 | H | F | CH₂CH₂F |
| n-C₃H₇ | | F | F | CH₂CH₂F |
| n-C₅H₁₁ | 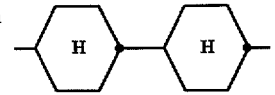 | H | H | CH₂CH₂F |

| R¹ | −(A¹−Z¹)ₘ−A²−Z²− | L¹ | L² | R² |
|---|---|---|---|---|
| n-C₅H₁₁ | 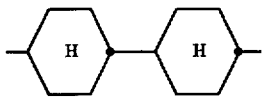 | H | F | CH₂CH₂F |
| n-C₅H₁₁ | 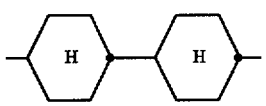 | F | F | CH₂CH₂F |
| C₂H₅ | 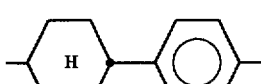 | H | H | CH₂CH₂F |
| C₂H₅ | 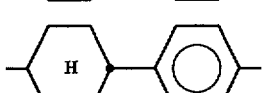 | H | F | CH₂CH₂F |
| C₂H₅ |  | F | F | CH₂CH₂F |
| n-C₃H₇ | 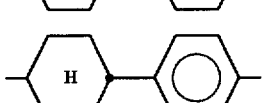 | H | H | CH₂CH₂F |
| n-C₃H₇ |  | H | F | CH₂CH₂F |
| n-C₃H₇ |  | F | F | CH₂CH₂F |
| n-C₅H₁₁ |  | H | H | CH₂CH₂F |
| n-C₅H₁₁ |  | H | F | CH₂CH₂F |
| n-C₅H₁₁ |  | F | F | CH₂CH₂F |
| C₂H₅ |  | H | H | CH₂CH₂F |
| C₂H₅ | 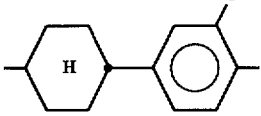 | H | F | CH₂CH₂F |
| C₂H₅ |  | F | F | CH₂CH₂F |
| n-C₃H₇ |  | H | H | CH₂CH₂F |
| n-C₃H₇ | 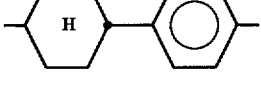 | H | F | CH₂CH₂F |
| n-C₃H₇ | 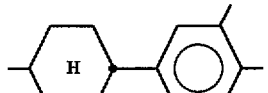 | F | F | CH₂CH₂F |
| n-C₅H₁₁ |  | H | H | CH₂CH₂F |
| n-C₅H₁₁ | 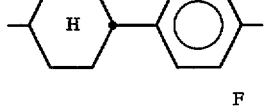 | H | F | CH₂CH₂F |
| n-C₅H₁₁ | 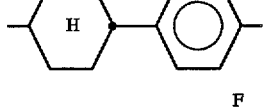 | F | F | CH₂CH₂F |
| C₂H₅ | 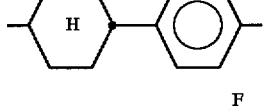 | H | H | CH₂CH₂F |
| C₂H₅ | 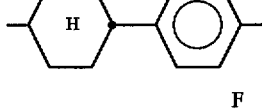 | H | F | CH₂CH₂F |
| C₂H₅ | 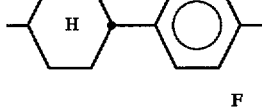 | F | F | CH₂CH₂F |
| n-C₃H₇ | 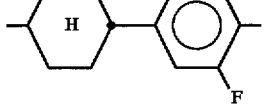 | H | H | CH₂CH₂F |

-continued

| R¹ | −(A¹−Z¹)ₘ−A²−Z²− | L¹ | L² | R² |
|---|---|---|---|---|
| n-C₃H₇ |  | H | F | CH₂CH₂F |
| n-C₃H₇ | 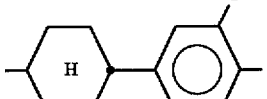 | F | F | CH₂CH₂F |
| n-C₅H₁₁ |  | H | H | CH₂CH₂F |
| n-C₅H₁₁ | 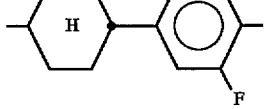 | H | F | CH₂CH₂F |
| n-C₅H₁₁ | 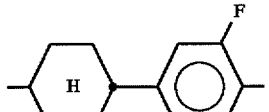 | F | F | CH₂CH₂F |
| n-C₃H₇ |  | H | H | CH₂CH₂F |
| n-C₃H₇ | 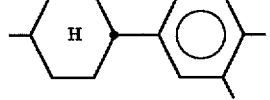 | H | F | CH₂CH₂F |
| n-C₃H₇ | 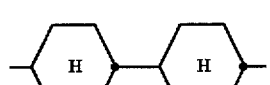 | F | F | CH₂CH₂F |
| n-C₅H₁₁ | 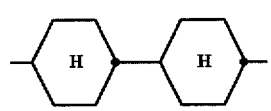 | H | H | CH₂CH₂F |
| n-C₅H₁₁ | 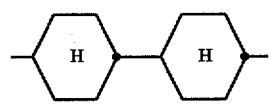 | H | F | CH₂CH₂F |
| n-C₅H₁₁ | 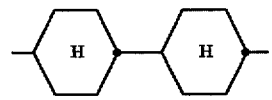 | F | F | CH₂CH₂F |
| n-C₃H₇ | 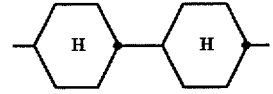 | H | H | CH₂CH₂F |
| n-C₃H₇ | 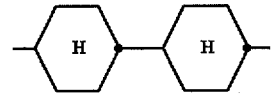 | H | F | CH₂CH₂F |
| n-C₃H₇ | 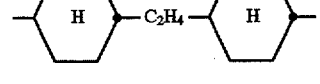 | F | F | CH₂CH₂F |
| n-C₅H₁₁ | 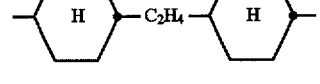 | H | H | CH₂CH₂F |
| n-C₅H₁₁ | 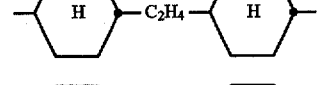 | H | F | CH₂CH₂F |
| n-C₅H₁₁ | 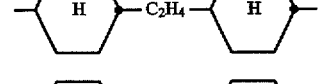 | F | F | CH₂CH₂F |
| C₂H₅ | 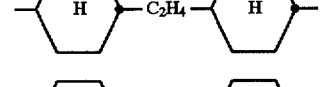 | H | H | CH₂CH₂F |
| n-C₃H₇ | 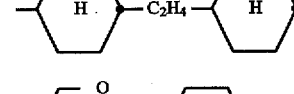 | H | F | CH₂CH₂F |
| n-C₅H₁₁ | 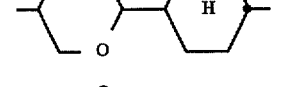 | F | F | CH₂CH₂F |
| C₂H₅ | 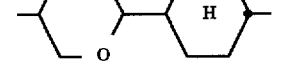 | H | H | CH₂CH₂F |
| n-C₃H₇ | 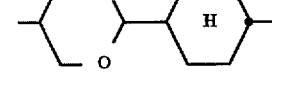 | H | F | CH₂CH₂F |
| n-C₅H₁₁ | 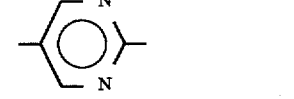 | F | F | CH₂CH₂F |
| n-C₃H₇ | 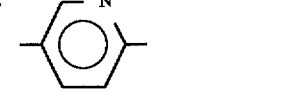 | F | F | CH₂CH₂F |
| C₂H₅ | 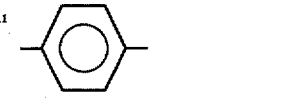 | H | H | C₂F₅ |

| R¹ | −(A¹−Z¹)ₘ−A²−Z²− | L¹ | L² | R² |
|---|---|---|---|---|
| C₂H₅ | [Cy]−[Cy] | H | F | C₂F₅ |
| C₂H₅ | [Cy]−[Cy] | F | F | C₂F₅ |
| n-C₃H₇ | [Cy]−[Cy] | H | H | C₂F₅ |
| n-C₃H₇ | [Cy]−[Cy] | H | F | C₂F₅ |
| n-C₃H₇ | [Cy]−[Cy] | F | F | C₂F₅ |
| n-C₅H₁₁ | [Cy]−[Cy] | H | H | C₂F₅ |
| n-C₅H₁₁ | [Cy]−[Cy] | H | F | C₂F₅ |
| n-C₅H₁₁ | [Cy]−[Cy] | F | F | C₂F₅ |
| C₂H₅ | [Cy]−[Ph] | H | H | C₂F₅ |
| C₂H₅ | [Cy]−[Ph] | H | F | C₂F₅ |
| C₂H₅ | [Cy]−[Ph] | F | F | C₂F₅ |
| n-C₃H₇ | [Cy]−[Ph] | H | H | C₂F₅ |
| n-C₃H₇ | [Cy]−[Ph] | H | F | C₂F₅ |
| n-C₃H₇ | [Cy]−[Ph] | F | F | C₂F₅ |
| n-C₅H₁₁ | [Cy]−[Ph] | H | H | C₂F₅ |
| n-C₅H₁₁ | [Cy]−[Ph] | H | F | C₂F₅ |
| n-C₅H₁₁ | [Cy]−[Ph] | F | F | C₂F₅ |
| C₂H₅ | [Cy]−[Ph(3-F)] | H | H | C₂F₅ |
| C₂H₅ | [Cy]−[Ph(3-F)] | H | F | C₂F₅ |
| C₂H₅ | [Cy]−[Ph(3-F)] | F | F | C₂F₅ |
| n-C₃H₇ | [Cy]−[Ph(3-F)] | H | H | C₂F₅ |
| n-C₃H₇ | [Cy]−[Ph(3-F)] | H | F | C₂F₅ |
| n-C₃H₇ | [Cy]−[Ph(3-F)] | F | F | C₂F₅ |
| n-C₅H₁₁ | [Cy]−[Ph(3-F)] | H | H | C₂F₅ |
| n-C₅H₁₁ | [Cy]−[Ph(3-F)] | H | F | C₂F₅ |
| n-C₅H₁₁ | [Cy]−[Ph(3-F)] | F | F | C₂F₅ |

| R¹ | −(A¹−Z¹)ₘ−A²−Z²− | L¹ | L² | R² |
|---|---|---|---|---|
| C₂H₅ | [Cy-H]—[Ph, 3-F, 4-F] | H | H | C₂F₅ |
| C₂H₅ | [Cy-H]—[Ph, 3-F, 4-F] | H | F | C₂F₅ |
| C₂H₅ | [Cy-H]—[Ph, 3-F, 4-F] | F | F | C₂F₅ |
| n-C₃H₇ | [Cy-H]—[Ph, 3-F, 4-F] | H | H | C₂F₅ |
| n-C₃H₇ | [Cy-H]—[Ph, 3-F, 4-F] | H | F | C₂F₅ |
| n-C₃H₇ | [Cy-H]—[Ph, 3-F, 4-F] | F | F | C₂F₅ |
| n-C₅H₁₁ | [Cy-H]—[Ph, 3-F, 4-F] | H | H | C₂F₅ |
| n-C₅H₁₁ | [Cy-H]—[Ph, 3-F, 4-F] | H | F | C₂F₅ |
| n-C₅H₁₁ | [Cy-H]—[Ph, 2-F, 3-F] | F | F | C₂F₅ |
| n-C₃H₇ | [Cy-H]—[Cy-H]—C₂H₄— | H | H | C₂F₅ |
| n-C₃H₇ | [Cy-H]—[Cy-H]—C₂H₄— | H | F | C₂F₅ |
| n-C₃H₇ | [Cy-H]—[Cy-H]—C₂H₄— | F | F | C₂F₅ |
| n-C₅H₁₁ | [Cy-H]—[Cy-H]—C₂H₄— | H | H | C₂F₅ |
| n-C₅H₁₁ | [Cy-H]—[Cy-H]—C₂H₄— | H | F | C₂F₅ |
| n-C₅H₁₁ | [Cy-H]—[Cy-H]—C₂H₄— | F | F | C₂F₅ |
| n-C₃H₇ | [Cy-H]—C₂H₄—[Cy-H] | H | H | C₂F₅ |
| n-C₃H₇ | [Cy-H]—C₂H₄—[Cy-H] | H | F | C₂F₅ |
| n-C₃H₇ | [Cy-H]—C₂H₄—[Cy-H] | F | F | C₂F₅ |
| n-C₅H₁₁ | [Cy-H]—C₂H₄—[Cy-H] | H | H | C₂F₅ |
| n-C₅H₁₁ | [Cy-H]—C₂H₄—[Cy-H] | H | F | C₂F₅ |
| n-C₅H₁₁ | [Cy-H]—C₂H₄—[Cy-H] | F | F | C₂F₅ |
| C₂H₅ | [dioxane]—[Cy-H] | H | H | C₂F₅ |

-continued

| R¹ | —(A¹—Z¹)ₘ—A²—Z²— | L¹ | L² | R² |
|---|---|---|---|---|
| n-C₃H₇ | cyclohexyl-O-C(=O)-[H]phenyl | H | F | C₂F₅ |
| n-C₅H₁₁ | cyclohexyl-O-C(=O)-[H]phenyl | F | F | C₂F₅ |
| C₂H₅ | pyrimidine | H | H | C₂F₅ |
| n-C₃H₇ | pyridine | H | F | C₂F₅ |
| n-C₅H₁₁ | phenyl | F | F | C₂F₅ |
| n-C₃H₇ | [H]cyclohexyl | F | F | C₂F₅ |
| C₂H₅ | [H]-[H] bicyclohexyl | H | H | CH₂C₂F₅ |
| C₂H₅ | [H]-[H] bicyclohexyl | H | F | CH₂C₂F₅ |
| C₂H₅ | [H]-[H] bicyclohexyl | F | F | CH₂C₂F₅ |
| n-C₃H₇ | [H]-[H] bicyclohexyl | H | H | CH₂C₂F₅ |
| n-C₃H₇ | [H]-[H] bicyclohexyl | H | F | CH₂C₂F₅ |
| n-C₃H₇ | [H]-[H] bicyclohexyl | F | F | CH₂C₂F₅ |
| n-C₅H₁₁ | [H]-[H] bicyclohexyl | H | H | CH₂C₂F₅ |
| n-C₅H₁₁ | [H]-[H] bicyclohexyl | H | F | CH₂C₂F₅ |

-continued

| R¹ | —(A¹—Z¹)ₘ—A²—Z²— | L¹ | L² | R² |
|---|---|---|---|---|
| n-C₅H₁₁ | [H]-[H] bicyclohexyl | F | F | CH₂C₂F₅ |
| C₂H₅ | [H]-phenyl | H | H | CH₂C₂F₅ |
| C₂H₅ | [H]-phenyl | H | F | CH₂C₂F₅ |
| C₂H₅ | [H]-phenyl | F | F | CH₂C₂F₅ |
| n-C₃H₇ | [H]-phenyl | H | H | CH₂C₂F₅ |
| n-C₃H₇ | [H]-phenyl | H | F | CH₂C₂F₅ |
| n-C₃H₇ | [H]-phenyl | F | F | CH₂C₂F₅ |
| n-C₅H₁₁ | [H]-phenyl | H | H | CH₂C₂F₅ |
| n-C₅H₁₁ | [H]-phenyl | H | F | CH₂C₂F₅ |
| n-C₅H₁₁ | [H]-phenyl | F | F | CH₂C₂F₅ |
| C₂H₅ | [H]-phenyl(F) | H | H | CH₂C₂F₅ |
| C₂H₅ | [H]-phenyl(F) | H | F | CH₂C₂F₅ |
| C₂H₅ | [H]-phenyl(F) | F | F | CH₂C₂F₅ |

| R¹ | −(A¹−Z¹)ₘ−A²−Z²− | L¹ | L² | R² |
|---|---|---|---|---|
| n-C₃H₇ | Cy−Ph(3-F)− | H | H | CH₂C₂F₅ |
| n-C₃H₇ | Cy−Ph(3-F)− | H | F | CH₂C₂F₅ |
| n-C₃H₇ | Cy−Ph(3-F)− | F | F | CH₂C₂F₅ |
| n-C₅H₁₁ | Cy−Ph(3-F)− | H | H | CH₂C₂F₅ |
| n-C₅H₁₁ | Cy−Ph(3-F)− | H | F | CH₂C₂F₅ |
| n-C₅H₁₁ | Cy−Ph(3-F)− | F | F | CH₂C₂F₅ |
| C₂H₅ | Cy−Ph(3,5-F₂)− | H | H | CH₂C₂F₅ |
| C₂H₅ | Cy−Ph(3,5-F₂)− | H | F | CH₂C₂F₅ |
| C₂H₅ | Cy−Ph(3,5-F₂)− | F | F | CH₂C₂F₅ |
| n-C₃H₇ | Cy−Ph(3,5-F₂)− | H | H | CH₂C₂F₅ |
| n-C₃H₇ | Cy−Ph(3,5-F₂)− | H | F | CH₂C₂F₅ |
| n-C₃H₇ | Cy−Ph(3,5-F₂)− | F | F | CH₂C₂F₅ |
| n-C₅H₁₁ | Cy−Ph(3,5-F₂)− | H | H | CH₂C₂F₅ |
| n-C₅H₁₁ | Cy−Ph(3,5-F₂)− | H | F | CH₂C₂F₅ |
| n-C₅H₁₁ | Cy−Ph(3,5-F₂)− | F | F | CH₂C₂F₅ |
| n-C₃H₇ | Cy−Cy−C₂H₄− | H | H | CH₂C₂F₅ |
| n-C₃H₇ | Cy−Cy−C₂H₄− | H | F | CH₂C₂F₅ |
| n-C₃H₇ | Cy−Cy−C₂H₄− | F | F | CH₂C₂F₅ |
| n-C₅H₁₁ | Cy−Cy−C₂H₄− | H | H | CH₂C₂F₅ |
| n-C₅H₁₁ | Cy−Cy−C₂H₄− | H | F | CH₂C₂F₅ |
| n-C₅H₁₁ | Cy−Cy−C₂H₄− | F | F | CH₂C₂F₅ |

| R¹ | —(A¹—Z¹)ₘ—A²—Z²— | L¹ | L² | R² |
|---|---|---|---|---|
| n-C₃H₇ | 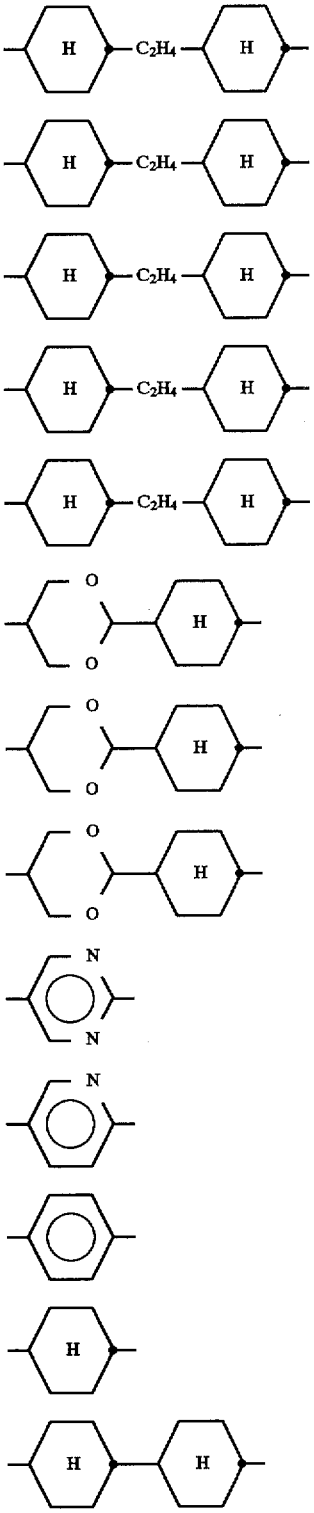 | H | H | CH₂C₂F₅ |
| n-C₃H₇ | 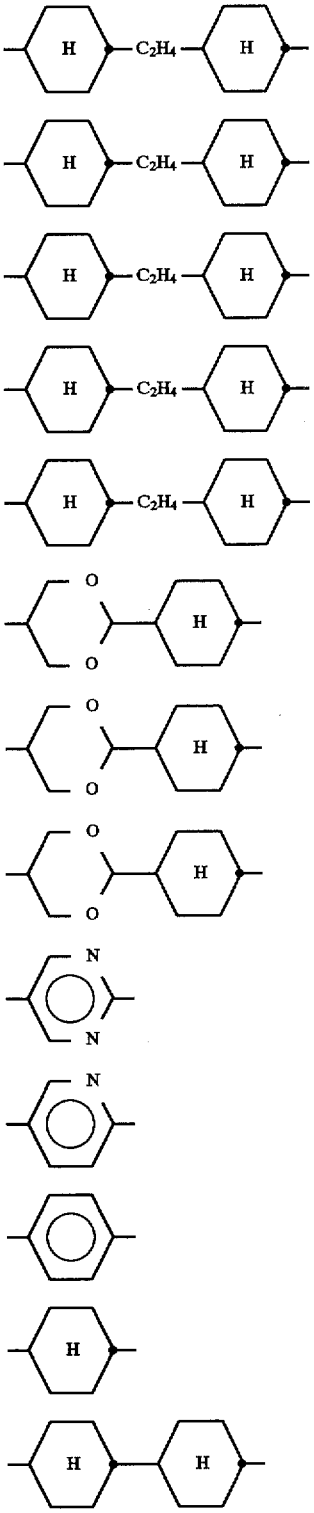 | H | F | CH₂C₂F₅ |
| n-C₃H₇ | 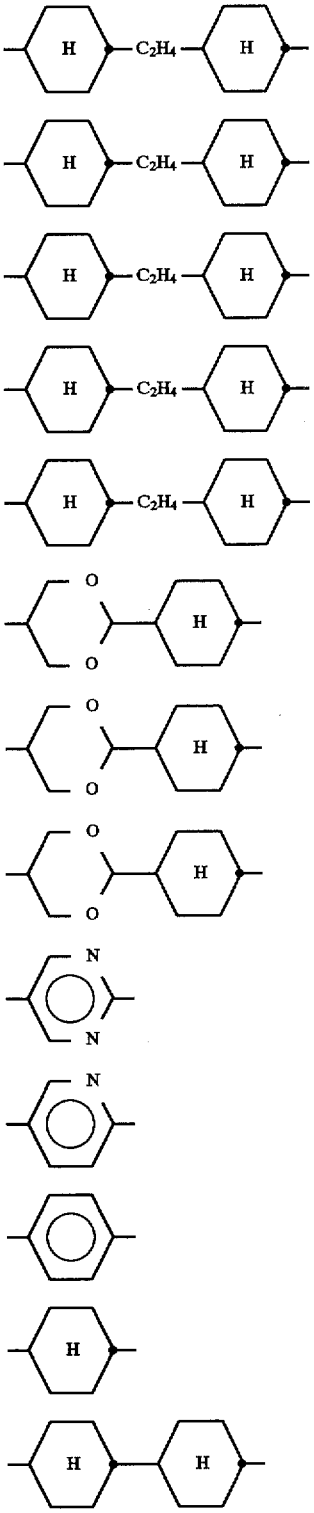 | F | F | CH₂C₂F₅ |
| n-C₅H₁₁ | 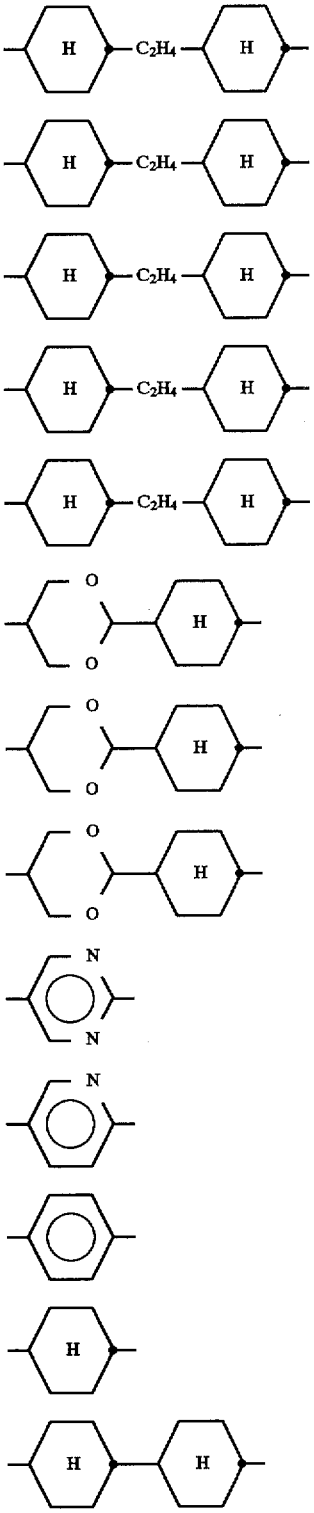 | H | H | CH₂C₂F₅ |
| n-C₅H₁₁ | 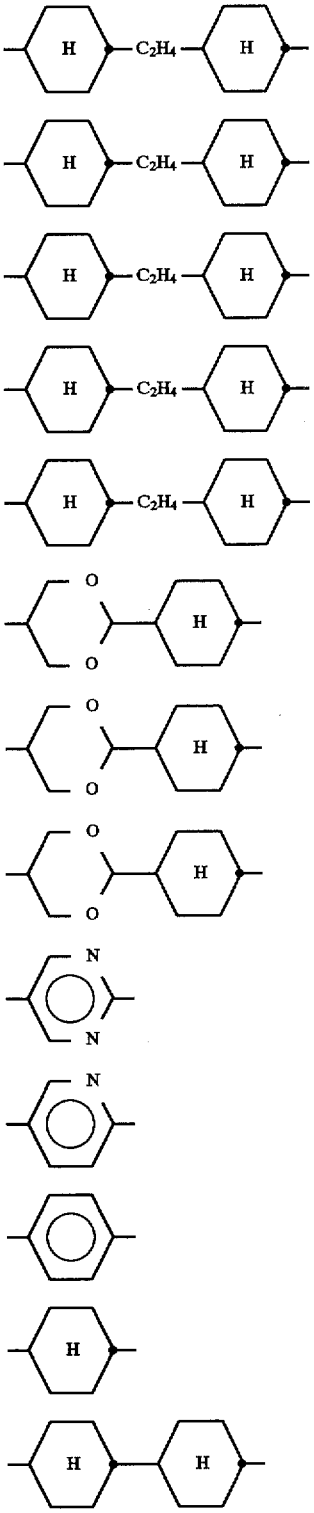 | H | F | CH₂C₂F₅ |
| n-C₅H₁₁ | 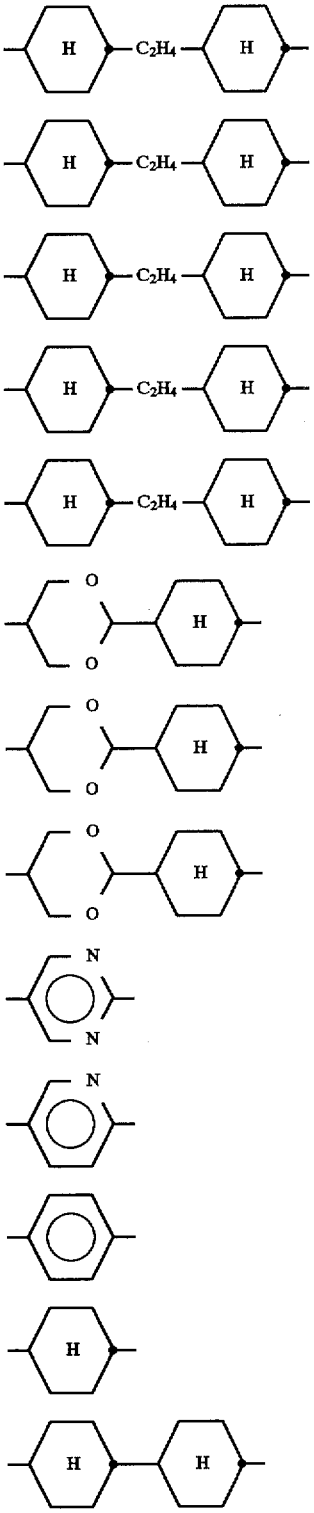 | F | F | CH₂C₂F₅ |
| C₂H₅ | 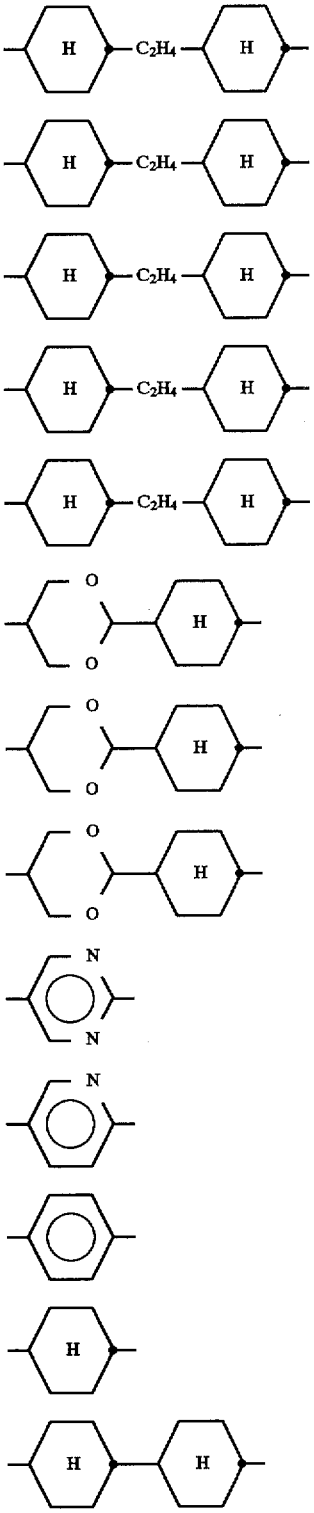 | H | H | CH₂C₂F₅ |
| n-C₃H₇ | 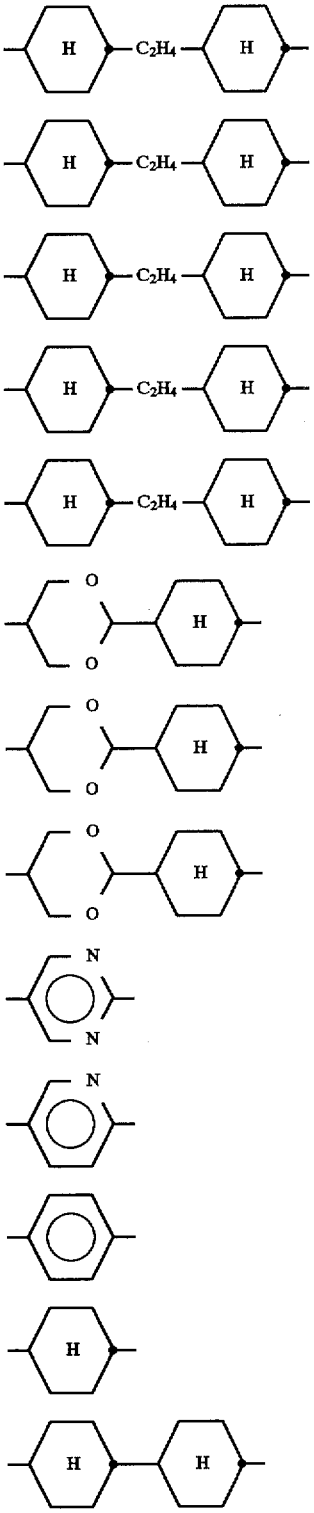 | H | F | CH₂C₂F₅ |
| n-C₅H₁₁ | 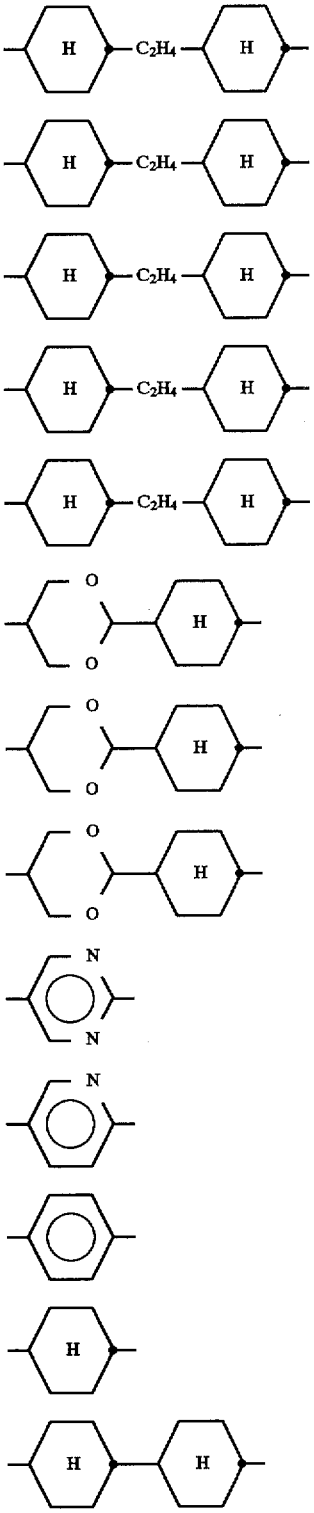 | F | F | CH₂C₂F₅ |
| C₂H₅ | 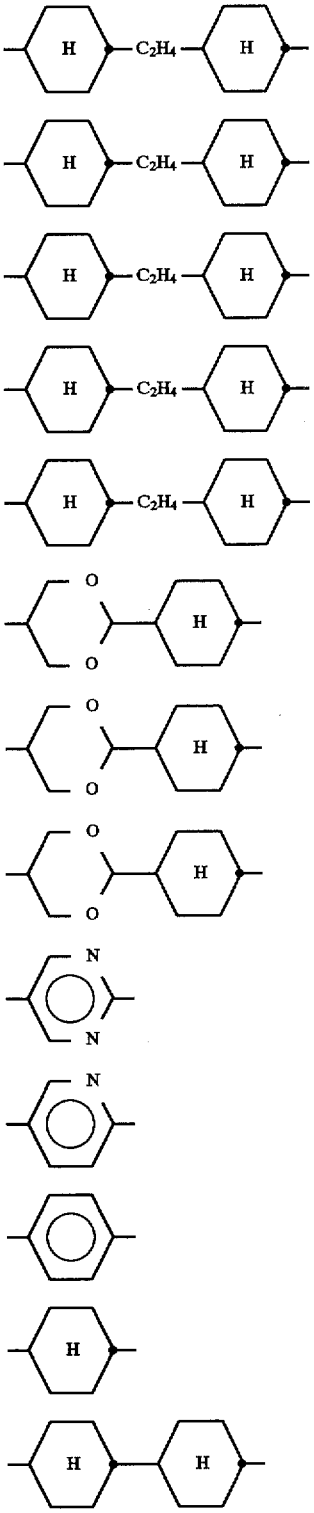 | H | H | CH₂C₂F₅ |
| n-C₃H₇ | 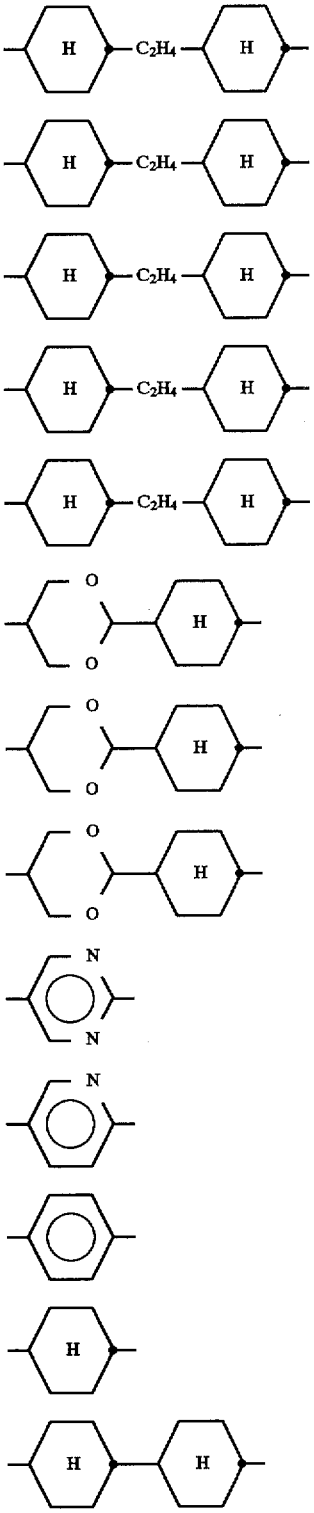 | H | F | CH₂C₂F₅ |
| n-C₅H₁₁ | 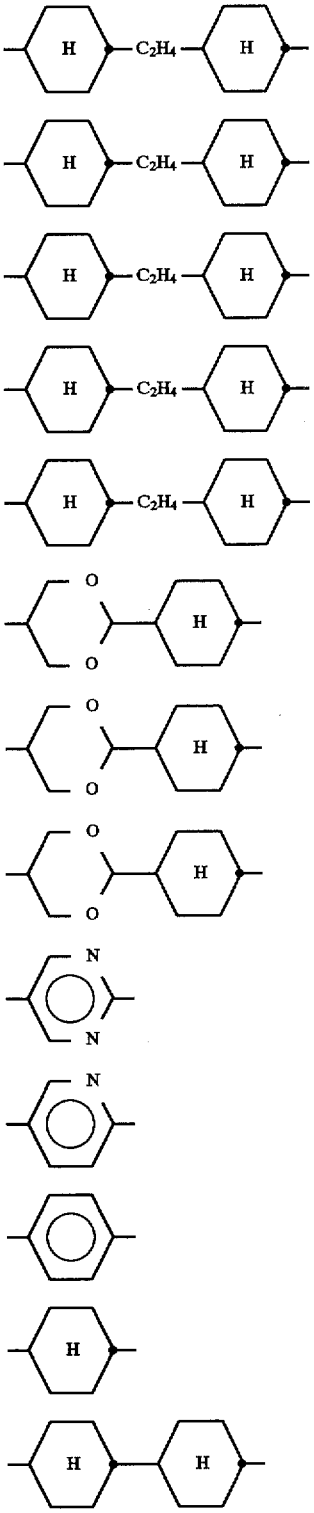 | F | F | CH₂C₂F₅ |
| n-C₃H₇ | 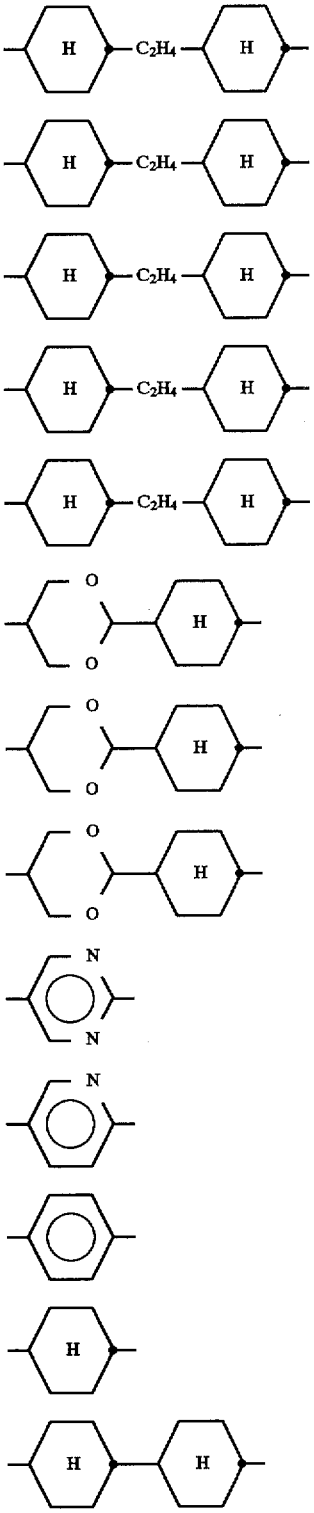 | F | F | CH₂C₂F₅ |
| n-C₃H₇ | 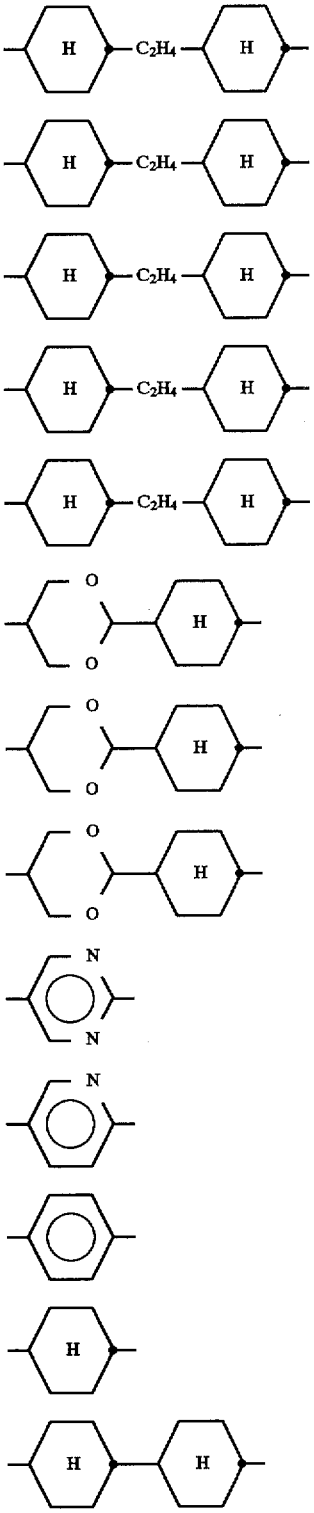 | H | H | C₂H₅ |

| R¹ | —(A¹—Z¹)ₘ—A²—Z²— | L¹ | L² | R² |
|---|---|---|---|---|
| n-C₃H₇ | 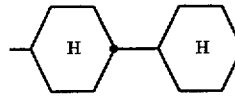 | H | F | C₂H₅ |
| n-C₃H₇ | 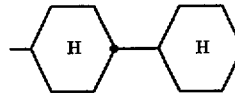 | F | F | C₂H₅ |
| n-C₅H₁₁ | 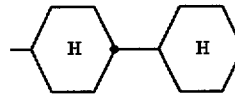 | H | H | C₂H₅ |
| n-C₅H₁₁ | 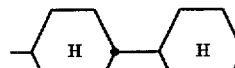 | H | F | C₂H₅ |
| n-C₅H₁₁ | 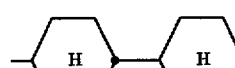 | F | F | C₂H₅ |
| n-C₃H₇ |  | H | H | C₂H₅ |
| n-C₃H₇ |  | H | F | C₂H₅ |
| n-C₃H₇ | 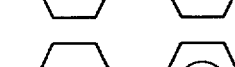 | F | F | C₂H₅ |
| n-C₅H₁₁ | 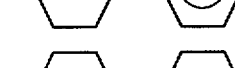 | H | H | C₂H₅ |
| n-C₅H₁₁ |  | H | F | C₂H₅ |
| n-C₅H₁₁ |  | F | F | C₂H₅ |
| n-C₃H₇ | 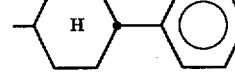 | H | H | C₂H₅ |
| n-C₃H₇ | 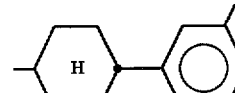 | H | F | C₂H₅ |
| n-C₃H₇ |  | F | F | C₂H₅ |

-continued

| R¹ | −(A¹−Z¹)ₘ−A²−Z²− | L¹ | L² | R² |
|---|---|---|---|---|
| n-C₅H₁₁ |  | H | H | C₂H₅ |
| n-C₅H₁₁ | | H | F | C₂H₅ |
| n-C₅H₁₁ | | F | F | C₂H₅ |
| n-C₃H₇ | | H | H | C₂H₅ |
| n-C₃H₇ | | H | F | C₂H₅ |
| n-C₃H₇ | | F | F | C₂H₅ |
| n-C₅H₁₁ | | H | H | C₂H₅ |
| n-C₅H₁₁ | | H | F | C₂H₅ |
| n-C₅H₁₁ | | F | F | C₂H₅ |

-continued

| R¹ | −(A¹−Z¹)ₘ−A²−Z²− | L¹ | L² | R² |
|---|---|---|---|---|
| n-C₃H₇ |  | H | H | C₂H₅ |
| n-C₃H₇ | | H | F | C₂H₅ |
| n-C₃H₇ | | F | F | C₂H₅ |
| n-C₅H₁₁ | | H | H | C₂H₅ |
| n-C₅H₁₁ | | H | F | C₂H₅ |
| n-C₅H₁₁ | | F | F | C₂H₅ |
| n-C₃H₇ | 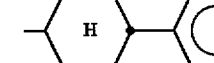 | H | H | C₂H₅ |
| n-C₃H₇ | | H | F | C₂H₅ |
| n-C₃H₇ | | F | F | C₂H₅ |
| n-C₅H₁₁ | | H | H | C₂H₅ |
| n-C₅H₁₁ | | H | F | C₂H₅ |
| n-C₅H₁₁ | | F | F | C₂H₅ |
| C₂H₅ | 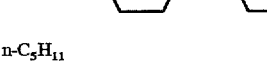 | H | H | C₂H₅ |
| n-C₃H₇ | | H | F | C₂H₅ |

| R¹ | −(A¹−Z¹)ₘ−A²−Z²− | L¹ | L² | R² |
|---|---|---|---|---|
| n-C₅H₁₁ | 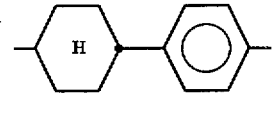 | F | F | C₂H₅ |
| C₂H₅ | 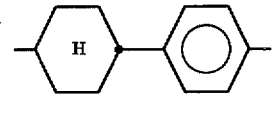 | H | H | C₂H₅ |
| n-C₃H₇ | 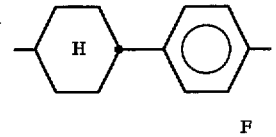 | H | F | C₂H₅ |
| n-C₅H₁₁ | 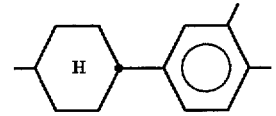 | F | F | C₂H₅ |
| n-C₃H₇ |  | F | F | C₂H₅ |
| n-C₃H₇ |  | H | H | C₃H₇ |
| n-C₃H₇ | 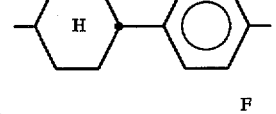 | H | F | C₃H₇ |
| n-C₃H₇ | 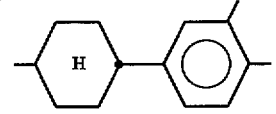 | F | F | C₃H₇ |
| n-C₅H₁₁ | 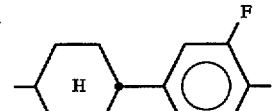 | H | H | C₃H₇ |
| n-C₅H₁₁ |  | H | F | C₃H₇ |
| n-C₅H₁₁ | 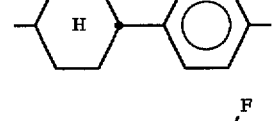 | F | F | C₃H₇ |
| n-C₃H₇ | 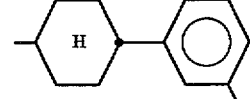 | H | H | C₃H₇ |
| n-C₃H₇ | 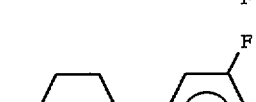 | H | F | C₃H₇ |
| n-C₃H₇ | | F | F | C₃H₇ |
| n-C₅H₁₁ | | H | H | C₃H₇ |
| n-C₅H₁₁ | | H | F | C₃H₇ |
| n-C₅H₁₁ | | F | F | C₃H₇ |
| n-C₃H₇ | | H | H | C₃H₇ |
| n-C₃H₇ | | H | F | C₃H₇ |
| n-C₃H₇ | | F | F | C₃H₇ |
| n-C₅H₁₁ | | H | H | C₃H₇ |
| n-C₅H₁₁ | | H | F | C₃H₇ |
| n-C₅H₁₁ | | F | F | C₃H₇ |
| n-C₃H₇ | | H | H | C₃H₇ |
| n-C₃H₇ | | H | F | C₃H₇ |

| $R^1$ | $-(A^1-Z^1)_m-A^2-Z^2-$ | $L^1$ | $L^2$ | $R^2$ |
|---|---|---|---|---|
| n-$C_3H_7$ | cyclohexyl-phenyl (3,4-diF) | F | F | $C_3H_7$ |
| n-$C_5H_{11}$ | cyclohexyl-phenyl (4-F) | H | H | $C_3H_7$ |
| n-$C_5H_{11}$ | cyclohexyl-phenyl (3,4-diF) | H | F | $C_3H_7$ |
| n-$C_5H_{11}$ | cyclohexyl-phenyl (3,4,5-triF) | F | F | $C_3H_7$ |
| n-$C_3H_7$ | cyclohexyl-cyclohexyl-$C_2H_4-$ | H | H | $C_3H_7$ |
| n-$C_3H_7$ | cyclohexyl-cyclohexyl-$C_2H_4-$ | H | F | $C_3H_7$ |
| n-$C_3H_7$ | cyclohexyl-cyclohexyl-$C_2H_4-$ | F | F | $C_3H_7$ |
| n-$C_5H_{11}$ | cyclohexyl-cyclohexyl-$C_2H_4-$ | H | H | $C_3H_7$ |
| n-$C_5H_{11}$ | cyclohexyl-cyclohexyl-$C_2H_4-$ | H | F | $C_3H_7$ |
| n-$C_5H_{11}$ | cyclohexyl-cyclohexyl-$C_2H_4-$ | F | F | $C_3H_7$ |
| n-$C_3H_7$ | cyclohexyl-$C_2H_4$-cyclohexyl- | H | H | $C_3H_7$ |
| n-$C_3H_7$ | cyclohexyl-$C_2H_4$-cyclohexyl- | H | F | $C_3H_7$ |
| n-$C_3H_7$ | cyclohexyl-$C_2H_4$-cyclohexyl- | F | F | $C_3H_7$ |
| n-$C_5H_{11}$ | cyclohexyl-$C_2H_4$-cyclohexyl- | H | H | $C_3H_7$ |
| n-$C_5H_{11}$ | cyclohexyl-$C_2H_4$-cyclohexyl- | H | F | $C_3H_7$ |
| n-$C_5H_{11}$ | cyclohexyl-$C_2H_4$-cyclohexyl- | F | F | $C_3H_7$ |
| $C_2H_5$ | dioxanyl-cyclohexyl- | H | H | $C_3H_7$ |
| n-$C_3H_7$ | dioxanyl-cyclohexyl- | H | F | $C_3H_7$ |
| n-$C_5H_{11}$ | dioxanyl-cyclohexyl- | F | F | $C_3H_7$ |
| $C_2H_5$ | pyrimidinyl- | H | H | $C_3H_7$ |
| n-$C_3H_7$ | pyrimidinyl- | H | F | $C_3H_7$ |
| n-$C_5H_{11}$ | phenyl- | F | F | $C_3H_7$ |
| n-$C_3H_7$ | cyclohexyl- | F | F | $C_3H_7$ |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A partially fluorinated benzene compound of the formula I

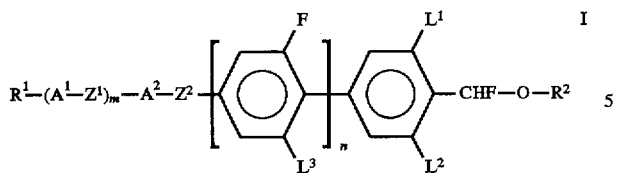

in which

R¹ is H, an alkyl or alkenyl radical having 1 to 15 carbon which is unsubstituted, monosubstituted by CN or CF₃, or monosubstituted to perhalo-substituted by halogen, where, optionally, one or more CH₂ groups in these radicals may each independently of one another be replaced by —O—, —S—,

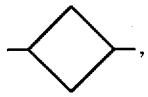

—CO—, —CO—O—, —O—CO— or —O—CO—O in such a way that O atoms are not linked directly to one another, A¹ and A² are each, independently of one another, (a) a trans-1,4-cyclohexylene radical in which, optionally, one or more non-adjacent CH₂ groups may be replaced by —O— and/or —S—, (b) a 1,4-phenylene radical in which, optionally, one or two CH groups may be replaced by N, (c) a radical from the group consisting of 1,4-cyclohexenylene, 1,4-bicyclo[2.2.2]octylene, piperidine-1,4-diyl, naphthalene-2,6-diyl, decahydronaphthalene-2,6-diyl and 1, 2, 3, 4-tetrahydronaphthalene-2,6-diyl, where the radicals (a) and (b) may further optionally be substituted by one or two fluorine atoms, Z¹ and Z² are each, independently of one another, —CO—O—, —O—CO—, —CH₂O—, —OCH₂—, —CH₂CH₂—, —CH=CH—, —C≡C—, —(CH)₄—, —CH=CH—CH₂CH₂— or a single bond, m is 0, 1 or 2, n is 0 or 1, L¹, L² and L³ are each, independently of one another, H or F, and R² is an alkyl radical having 1 to 6 carbon atoms which is unsubstituted or substituted by one or more fluorine atoms.

2. The compound of claim 1, which is a compound of the formula I1

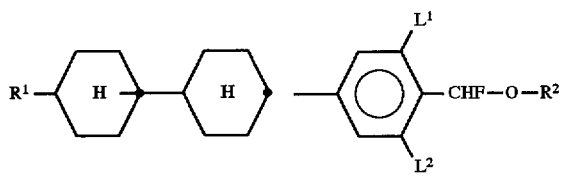

wherein R¹, L¹, L² and R² are as defined.

3. The compound of claim 1, which is a compound of the formula I3

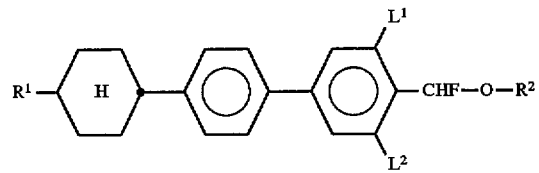

wherein R¹, L¹, L² and R² are as defined.

4. The compound of claim 1, which is a compound of the formula

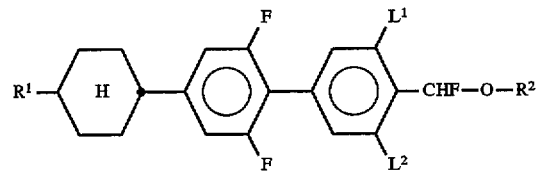

in which R¹, R², L¹, L² and L³ are as defined.

5. A compound of claim 1, wherein R² is —CF₃, —CH₂CF₃, —CH₂CHF₂, —CH₂CH₂F, —CF₂CHF₂, —CF₂CH₂F, —CHFCF₃, —CF₂CF₃, —CH₂—CF₂—CHF₂, —CH₂C₂F₅, —CHFCHF₂, —C₂H₅ or C₃H₇.

6. A liquid-crystalline medium comprising at least two liquid-crystalline components, wherein at least one component is a compound of the formula I of claim 1.

7. A liquid-crystal display element, comprising a liquid-crystalline medium according to claim 6.

8. A electrooptical display element, comprising, as dielectric, a liquid-crystalline medium according to claim 6.

9. The liquid-crystal display element of claim 7, wherein the display is based on the principle of the twisted cell, the guest-host effect, the effect of deformation of aligned phases or the effect of dynamic scattering.

10. A compound of claim 1 selected from one of the subformulae Ia to IK:

| | |
|---|---|
|  | Ia |
| 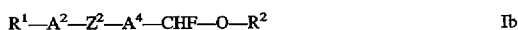 | Ib |
| 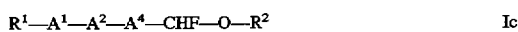 | Ic |
| 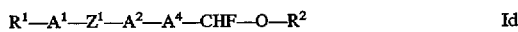 | Id |
| 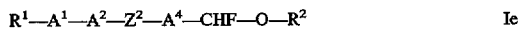 | Ie |
| 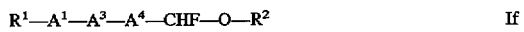 | If |
| 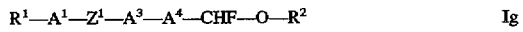 | Ig |
| 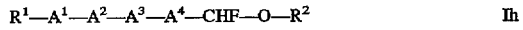 | Ih |
|  | Ii |
|  | Ij |
| 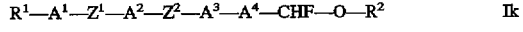 | Ik | wherein R¹, A¹, A², Z¹, Z² and R² are defined, $A^3$ is

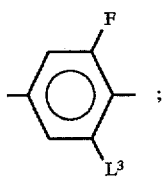;

$A^4$ is

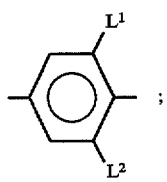;

where $L^1$, $L^2$ and $L^3$ are as defined.

11. A compound of claim 10, wherein $A^1$ and $A^2$ are each independently 1,4-cyclohexyl optionally mono- or di-substituted by F or CN, 1,4-cyclohexylene, 1,4-phenylene optionally mono- or di-substituted by F or CN, pyrimidine-2,5-diyl, pyridine-2,5-diyl or 1,3-dioxane-2,5-diyl.

12. A compound of claim 1, wherein $A^1$ and $A^2$ are independently

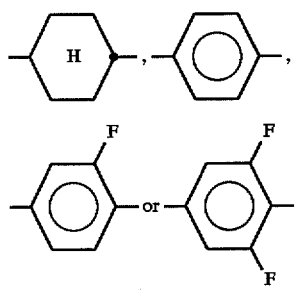

13. A compound of claim 1, wherein each of $Z^1$ and $Z^2$ are independently a single bond, —CO—O—, —O—CO— or —$CH_2CH_2$—.

14. A compound of claim 1, wherein m+n=1.

15. A compound of claim 1, wherein $R^1$ is alkyl or alkoxy of 2 to 7 carbon atoms.

16. A medium of claim 6, wherein the medium contains 1 to 40% by weight of compounds of the formula I.

17. A medium of claim 6, wherein the medium contains 45 to 90% by weight of compounds of the formula I.

18. A compound of the formula

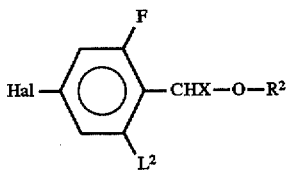

in which

Hal is Cl or Br,

X is Cl or F, $L^2$ is H or F, and $R^2$ is an alkyl radical having 1 to 6 carbon atoms which is unsubstituted or substituted by one or more fluorine atoms.

* * * * *